(12) United States Patent
Takahashi et al.

(10) Patent No.: US 9,072,791 B2
(45) Date of Patent: Jul. 7, 2015

(54) PHOTOSTABILIZED PHARMACEUTICAL COMPOSITIONS

(75) Inventors: Koichi Takahashi, Machida (JP); Tadashi Morikawa, Machida (JP); Tadao Yamazaki, Kita-ku (JP); Masaki Shibata, Gotenba (JP)

(73) Assignee: DENKI KAGAKU KOGYO KABUSHIKI KAISHA, Tokyo (JP)

( * ) Notice: Subject to any disclaimer, the term of this patent is extended or adjusted under 35 U.S.C. 154(b) by 78 days.

(21) Appl. No.: 13/121,852

(22) PCT Filed: Sep. 30, 2009

(86) PCT No.: PCT/JP2009/067018
§ 371 (c)(1),
(2), (4) Date: Jun. 10, 2011

(87) PCT Pub. No.: WO2010/038771
PCT Pub. Date: Apr. 8, 2010

(65) Prior Publication Data
US 2011/0245276 A1    Oct. 6, 2011

(30) Foreign Application Priority Data
Sep. 30, 2008    (JP) .................... 2008-252254

(51) Int. Cl.
| | | |
|---|---|---|
| *A01N 43/04* | (2006.01) | |
| *A61K 31/715* | (2006.01) | |
| *A01N 43/90* | (2006.01) | |
| *A61K 31/519* | (2006.01) | |
| *A61K 47/48* | (2006.01) | |
| *A61K 9/00* | (2006.01) | |
| *A61K 9/08* | (2006.01) | |
| *A61K 45/06* | (2006.01) | |

(52) U.S. Cl.
CPC ........... *A61K 47/4823* (2013.01); *A61K 9/0019* (2013.01); *A61K 9/08* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,303,676 | A * | 12/1981 | Balazs | 514/773 |
| 6,197,326 | B1 * | 3/2001 | Suzuki et al. | 424/426 |
| 6,346,519 | B1 * | 2/2002 | Petrus | 514/62 |
| 2002/0041437 | A1 * | 4/2002 | Cornelius | 359/361 |
| 2006/0040894 | A1 * | 2/2006 | Hunter et al. | 514/54 |
| 2007/0197465 | A1 * | 8/2007 | Ikeya et al. | 514/54 |
| 2008/0221062 | A1 * | 9/2008 | Miyamoto et al. | 514/54 |

FOREIGN PATENT DOCUMENTS

| | | |
|---|---|---|
| CA | 2047482 | 1/1992 |
| JP | 4-253924 | 9/1992 |
| JP | 2005-247803 | 9/2005 |
| WO | WO 94/25032 A1 | 11/1994 |
| WO | WO 2005/085294 A1 | 9/2005 |

OTHER PUBLICATIONS

Frati et al., Degradation of Hyaluronic Acid by Photosensitized Riboflavin In Vitro. Modulation of the Effect by Transition Metals, Radical Quenchers, and Metal Chelators, Free Radical Biology & Medicine, vol. 22, No. 7, pp. 1139-1144, (1997).*
Lapč,iik et al., "Photodegradation of Hyaluronic Acid and of the Vitreous Body," Gen. Physiol. Biophys. (1990) 9, 419-429.*
Templeton et al., "Implications of Photostability on the Manufacturing, Packaging, Storage and Testing of Formulated Pharamaceutical Products," Pharmaceutical Technology Mar. 2005, pp. 68-86.*
Darouiche, "Treatment of Infections Associated with Surgical Implants," The New England Journal of Medicine 350;14, Apr. 1, 2004.*
International Search Report issued Nov. 17, 2009, in PCT/JP2009/067018.
C. Chahidi, et al., "2,4-Diamino-6-Pteridinecarboxaldehyde and an Azobenzene Derivative Are Produced by UV Photodegradation of Methotrexate", Photochemistry and Photobiology, vol. 44, No. 2, 1986, pp. 231-233.
Usha P. Andley, et al., "Role of Singlet Oxygen in the Degradation of Hyaluronic Acid", Biochemical and Biophysical Research Communications, vol. 115, No. 3, Sep. 30, 1983, pp. 894-901.
Elena Frati, et al., "Degradation of Hyaluronic Acid by Photosensitized Riboflavin in Vitro. Modulation of the Effect by Transition Metals, Radical Quenchers, and Metal Chelators", Free Radical Biology & Medicine, vol. 22, No. 7, 1997, pp. 1139-1144.
Extended European Search Report issued Apr. 17, 2012 in patent application No. 09817803.1.

* cited by examiner

*Primary Examiner* — Craig Ricci
*Assistant Examiner* — Jared D Barsky
(74) *Attorney, Agent, or Firm* — Oblon, McClelland, Maier & Neustadt, L.L.P.

(57) ABSTRACT

A crosslinking reaction and a reaction for reducing molecular weight that take place in a hyaluronic acid-methotrexate conjugate upon irradiation with light are suppressed to improve the photostability of the conjugate. Specifically, a substance having a quenching effect and/or a radical scaveng effect is added to a pharmaceutical composition containing the hyaluronic acid-methotrexate conjugate.

9 Claims, 11 Drawing Sheets

Gel filtration

Reverse-phase

MALDI-TOFMS analysis of fraction F obtained in reverse-phase preparative chromatography Mass spectra of fraction F obtained from MALDI-TOFMS

PHOTOSTABILIZED PHARMACEUTICAL COMPOSITIONS

This application is a National Stage of PCT/JP09/067018 filed Sep. 30, 2009 and claims the benefit of JP 2008-252254 filed Sep. 30, 2008.

BACKGROUND ART

In the current aging society, the number of patients with joint diseases including osteoarthritis (hereinafter also referred to as OA) has been steadily increasing. The present inventors provided in the previous application a pharmaceutical composition that comprised a conjugate of hyaluronic acid (hereinafter also referred to as HA) and methotrexate (hereinafter also referred to as MTX) and which was useful as a therapeutic drug for joint diseases (WO05/85294). The conjugate is a remarkable compound in which the characteristic of HA that can be used as a safe intra-articular injection for joint diseases that is a potential substitute for steroid preparations is combined with the characteristic of MTX that is capable of suppressing synovitis.

Subsequent studies, however, have revealed that upon irradiation with light, this compound is prone to gel or experience a drop in molecular weight, i.e., its storage stability is not completely satisfactory. Under the circumstances, it is recommended that pharmaceutical compositions comprising the hyaluronic acid-methotrexate conjugate be stored in a cool dark space until they are taken out of it just before use. Alternatively, aluminum foil or its equivalent may be used to assure complete shielding of light. However, in medical settings such as hospitals, the pharmaceutical compositions, after taken out of the cold dark space or stripped of the light-shielding wrap, may often be left under light for several to ten-odd hours. Thus, the simple means of packaging the container of pharmaceuticals with the light-shielding material is not enough to ensure that the hyaluronic acid-methotrexate conjugate remains stable and an improvement in its photostability has been desired.

CITATION LIST

Patent Document

Patent Document 1: WO05/85294

SUMMARY OF INVENTION

Technical Problems

The present inventors studied the possible cause for the HA-MTX conjugate to become instable upon irradiation with light (the cause for the gelation and the drop in molecular weight) and came to presume that at least two reactions might be involved in the phenomenon of being instable under light.

In the first reaction, the pteridine ring (a) derived from the MTX residue is eliminated from the molecule of the hyaluronic acid-methotrexate conjugate upon irradiation with light (reaction A in FIG. 1), whereby an aminobenzoic acid portion (b) forms in the molecule of the conjugate, and two such aminobenzoic acid portions combine together to form an azo dimer (reaction B in FIG. 1). Consequently, hyaluronic acid molecules are crosslinked via the azo dimer.

This reaction mechanism is suggested by Examples 2 and 3 to be described later in this specification. Note that the azo dimer is also formed if the MTX molecule itself is irradiated with light (Photochemistry and Photobiology, vol. 44, No. 2, pp. 231-233, 1986; C. Chahide et al.) and this also supports the validity of the above-described reaction mechanism.

The thus created crosslinks are believed to cause the gelation of the hyaluronic acid-methotrexate conjugate.

In the second reaction, radical species that are produced upon irradiation with light act on the polymer chain of the hyaluronic acid in the hyaluronic acid-methotrexate conjugate, and this presumably causes the molecular weight of the conjugate to decrease.

An object, therefore, of the present invention is to suppress the above two reactions which take place in the hyaluronic acid-methotrexate conjugate upon irradiation with light, thereby improving the photostability of the conjugate.

Solution to Problem

The present inventors made intensive studies with a view to improving the photostability of the hyaluronic acid-methotrexate conjugate by suppressing the gelation and drop in molecular weight that would otherwise be caused by irradiation with light. As a result, they found that when a photostabilizer, specifically, a substance having the ability to absorb energy from a molecule in an excited state caused by irradiation with light (i.e., quenching effect) and/or the ability to scavenge radicals produced by irradiation with light (i.e., radical scavenging effect), was incorporated in a pharmaceutical composition containing the hyaluronic acid-methotrexate conjugate, the stability of the hyaluronic acid-methotrexate conjugate could be improved. These effects can also be applied to the conjugate of a hyaluronic acid derivative and methotrexate. The present invention has been accomplished on the basis of these findings.

Thus, the present invention relates to a photostabilized pharmaceutical composition comprising a conjugate of hyaluronic acid or a hyaluronic acid derivative and methotrexate or a salt of the conjugate, and a photostabilizer.

In another aspect, the present invention provides the above-described pharmaceutical composition which incorporates the photostabilizer in an amount of 0.01-30% (w/v).

In yet another aspect, the present invention also provides the above-described pharmaceutical composition in which the photostabilizer is a quencher or a radical scavenger. Preferably, the photostabilzier is both a quencher and a radical scavenger.

In another aspect, the present invention provides the above-described pharmaceutical composition in which the photostabilizer is a sulfur-containing inorganic acid, a sulfur-containing organic acid, an aromatic amino acid derivative or a hydroxybenzoic acid, or a salt thereof.

In still another aspect, the present invention provides a medicine comprising the above-described pharmaceutical composition as it is wrapped with a packaging material that at least blocks light over the entire wavelength region of light ranging from 320 to 430 nm, preferably over the entire wavelength region not exceeding 540 nm.

Advantageous Effects of Invention

According to the present invention, the photostability of the conjugate of hyaluronic acid or a hyaluronic acid derivative and methotrexate can be improved by adding a photostabilizer. In addition, there can be provided a pharmaceutical composition that is assured of satisfactory stability even if it is handled under the practice of clinical settings where there is a possibility that it might be left for long after it is stripped of the package. A further advantage of the present invention is

DESCRIPTION OF EMBODIMENTS

Figure 1:
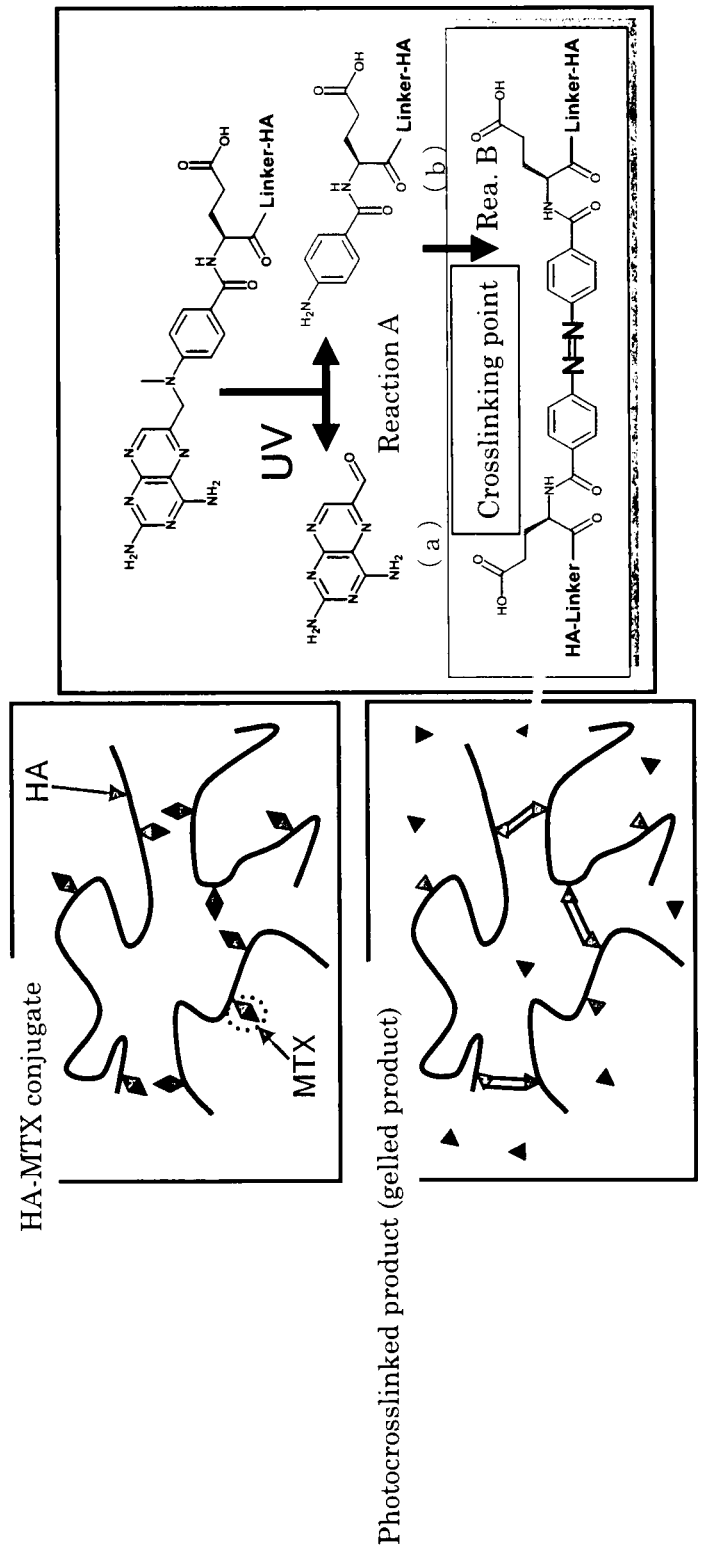
FIG. 1 shows the reactions that take place in the HA-MTX conjugate upon irradiation with light.

The present invention is described hereinafter in detail.

Hyaluronic Acid-Methotrexate Conjugate

The hyaluronic acid-methotrexate conjugate used herein refers to a compound having such a structure that the molecule of hyaluronic acid or a hyaluronic acid derivative and the methotrexate molecule are conjugated either directly or indirectly via a linker, or a salt of the compound. This conjugate is hereinafter also referred to as the "HA-MTX conjugate."

The term "hyaluronic acid" as used herein is not particularly limited but refers to a polymer of disaccharide consisting of glucuronic acid and N-acetylglucosamine, typically having an average molecular weight of 50,000 to 10,000,000 daltons. In the present invention, free hyaluronic acid or its salts may be employed. The salts of hyaluronic acid to be used in the present invention are not particularly limited but include, for example, sodium salt, potassium salt, calcium salt, aluminum salt, zinc salt, iron salt, ammonium salt, and tetrabutylammonium salt. Specific examples of hyaluronic acid or its salts and mixtures thereof include Suvenyl™ (manufactured and distributed by Chugai Pharmaceutical Co., Ltd.); Artz™ (manufactured by Seikagaku Corporation and distributed by Kaken Pharmaceutical Co., Ltd.); and Opegan™ (manufactured by Seikagaku Corporation and distributed by Santen Pharmaceutical Co., Ltd.) The term "hyaluronic acid derivative" as used in the present invention refers to a substance having a hyaluronic acid skeleton derived from hyaluronic acid. Hyaluronic acid derivatives are not particularly limited but include, for example, substances wherein one or more carboxyl groups in hyaluronic acid are esterified (e.g., benzyl esterified hyaluronic acid (trade name: Hyaff™, from Fidia Advanced Biopolymers)), substances obtained by crosslinking hyaluronic acid with formaldehyde to further increase its molecular weight (e.g., trade name: Synvisc™, from Biomatrix)), and acetylated hyaluronic acid obtained by acetylating one or more hydroxy groups in hyaluronic acid. The term "HA" as used in the following explanation shall mean hyaluronic acid or hyaluronic acid derivatives or salts thereof.

Since the HA-MTX conjugate of the invention should not impair the pain-eliminating effect of HA, a preferred HA-MTX conjugate is such that it retains comparable levels of molecular weight size and viscoelasticity to those of HA which has been clinically verified to have a pain-eliminating effect. Stated specifically, considering that an increased molecular weight leads to a higher viscoelasticity, rendering the handling difficult to perform, and also considering the effect of HA as a carrier in the living body, the HA-MTX conjugate preferably has a molecular weight of 600,000 to 6,000,000 daltons, more preferably 800,000 to 6,000,000 daltons, even more preferably 1,000,000 to 5,000,000 daltons.

Here, the molecular weights of the above-described starting material HA and the HA-MTX conjugate are determined by a method for calculating a viscosity-average molecular weight from a limiting viscosity. For limiting viscosity, a sample was dissolved in a 0.2 M NaCl aqueous solution and put into a Ubbelohde viscometer (product of KUSANO SCIENCE CORPORATION; Viscometer No. 0C), which was placed in a thermostatic chamber for measurement at 30° C. Calculation for conversion from limiting viscosity ([1]) to viscosity-average molecular weight (Mw) can be made using the following equation.

$$Mw=([\eta]/0.00036)^{1.282}$$

A suitable example of the HA-MTX conjugate that can be used in the present invention is described in WO05/85294 filed by the Applicant of the subject application.

It is specifically a HA-MTX conjugate in which HA has a carboxyl group in it conjugated with methotrexate via a linker containing a peptide chain consisting of 1 to 8 amino acids.

Preferably, the linker contains a peptide chain consisting of 1 to 8 amino acids and a $C_{2-20}$ alkylenediamine chain into which 1 to 5 oxygen atoms are optionally inserted and/or which is optionally substituted by a carboxyl group or a $C_{1-6}$ alkoxycarbonyl group.

More preferably, the methotrexate conjugated with the linker in the above-described HA-MTX conjugate is represented by formula (I), (II), (III), or (IV):

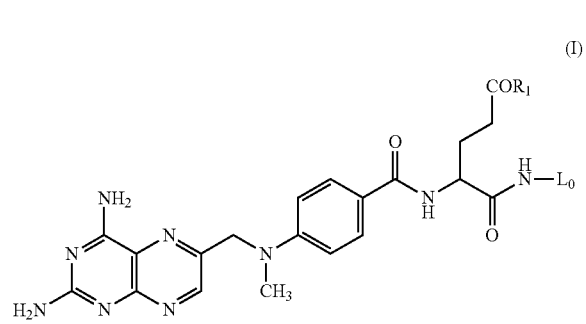

(II)

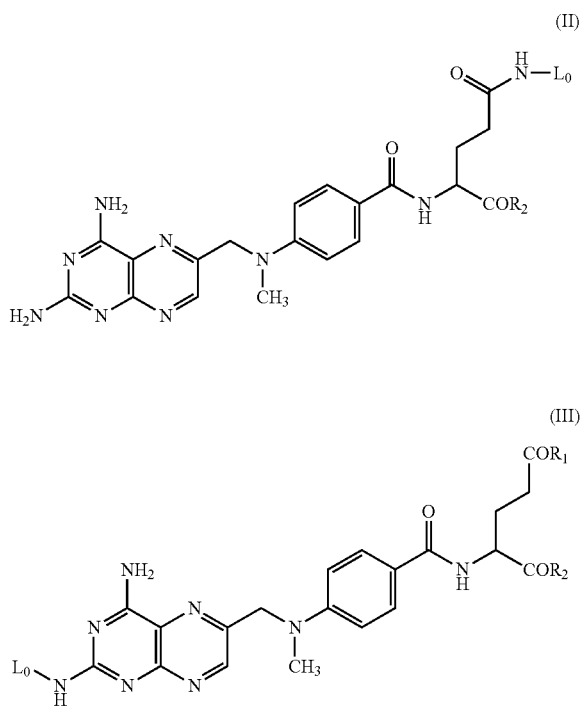

(III)

(IV)

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;

$L_0$ is the conjugating position of the linker.

Even more preferably, the linker containing a peptide chain in the above-described HA-MTX conjugate and the methotrexate conjugated with the linker is represented by formula (I') or (II'):

(I')

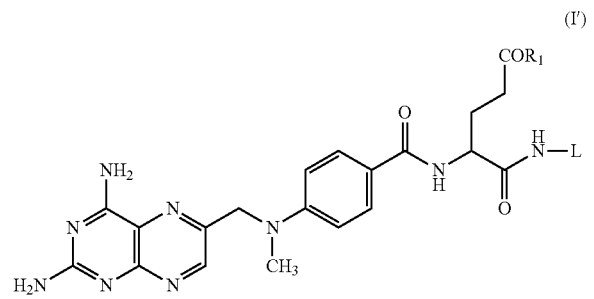

(II")

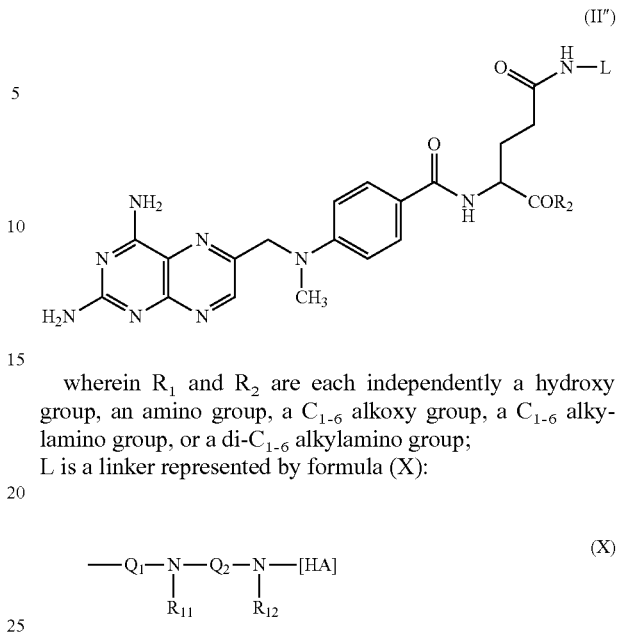

wherein $R_1$ and $R_2$ are each independently a hydroxy group, an amino group, a $C_{1-6}$ alkoxy group, a $C_{1-6}$ alkylamino group, or a di-$C_{1-6}$ alkylamino group;

L is a linker represented by formula (X):

$$-Q_1-\underset{R_{11}}{N}-Q_2-\underset{R_{12}}{N}-[HA] \qquad (X)$$

wherein $Q_1$ forms, together with —NH— binding thereto, a peptide chain consisting of 1 to 8 amino acids; the residues of amino acids contained in the peptide chain are each independently optionally substituted or protected by one or more groups selected from the group consisting of a $C_{1-6}$ alkyl group, a $C_{1-6}$ alkylcarbonyl group, a $C_{1-6}$ alkoxycarbonyl group, a formyl group, a $C_{1-6}$ alkylsulfonyl group, and a $C_{6-10}$ arylsulfonyl group; the amide bonds contained in the peptide chain are each independently optionally substituted on the nitrogen atom by one or more $C_{1-6}$ alkyl groups and/or $C_{1-6}$ alkylcarbonyl groups; and the carboxyl groups contained in the residues are each independently optionally converted to an amide group optionally substituted by one or two $C_{1-6}$ alkyl groups;

$R_{11}$ and $R_{12}$ are each independently a hydrogen atom or a $C_{1-6}$ alkyl group;

$Q_2$ is $C_{2-20}$ alkylene which optionally has 1 to 5 oxygen atoms inserted thereinto and/or which is optionally substituted by a carboxyl group or a $C_{1-6}$ alkoxycarbonyl group; and

[HA] represents the position of conjugation with hyaluronic acid, and the linker forms an amide bond with a carboxyl group contained in the HA.

The peptide chain in the linker to be used in a preferred mode of the present invention is composed of amino acids. Examples of the amino acids include natural α-amino acids such as glycine, alanine, serine, proline, valine, threonine, cysteine, leucine, isoleucine, asparagine, aspartic acid, lysine, glutamine, glutamic acid, methionine, histidine, phenylalanine, arginine, tyrosine, and tryptophan; non-natural α-amino acids such as an α-amino acid having an alkyl side chain (e.g., norvaline, norleucine, or t-leucine), alanine or glycine substituted by a cycloalkyl group (e.g., cyclopentylalanine, cyclohexylalanine, or cyclohexylglycine), and alanine or glycine substituted by an aryl group (e.g., pyridylalanine, thienylalanine, naphthylalanine, substituted phenylalanine, or phenylglycine); β-amino acids such as β-alanine, γ-amino acids such as γ-aminobutyric acid, and aminosulfonic acids such as taurine. Amino acids in the linker peptide of the present invention also include those whose residues are substituted or protected in an appropriate manner. For example, the functional group on the residue can be protected with a protective group. Protective groups that may be used for this purpose are well known in the art, and some examples of them are described herein at other paragraphs. Methods for introducing the respective substituents and protective groups, in particular, the protective groups, may be selected from among those that are well known in the art.

The linker may be composed of only amino acids, or may contain, inside or at the end of the peptide chain, a part derived from a compound other than amino acids. For example, the linkers include a linker which has a diamino compound such as alkylenediamine or oxaalkylenediamine or a dicarboxylic acid compound such as succinic acid linked inside or at the end of the peptide chain. When the linker contains a compound other than amino acids inside or at the end of the peptide chain and is linked to a carboxyl group in methotrexate (MTX) and a carboxyl group in HA, a diamino compound such as alkylenediamine or oxaalkylenediamine is preferably present at the end of the peptide chain; it is particularly preferred that ethylenediamine or 4,7,10-trioxa-1,13-tridecanediamine is present at the end of the peptide chain. The amino acids constituting the peptide chain are not particularly limited but they are preferably α-amino acids in view of affinity to protease; the end of the peptide chain containing linker at which it is conjugated with MTX is preferably an α-amino acid.

The number of amino acids constituting the peptide chain is not particularly limited but it is typically 1 to 8, preferably 1 to 6, more preferably 1 to 4. The residues of amino acids that constitute the peptide chain may each independently be substituted or protected by one or more groups in an appropriate manner. Such groups include, but are not limited to, $C_{1-6}$ alkyl groups, $C_{1-6}$ alkylcarbonyl groups, $C_{1-6}$ alkoxycarbonyl groups (e.g., a methoxycarbonyl group, an ethoxycarbonyl group, an (n- or i-)propyloxycarbonyl group, and an (n-, s-, or t-)butoxycarbonyl group), a formyl group, $C_{1-6}$ alkylsulfonyl groups (e.g., a methanesulfonyl group, an ethanesulfonyl group, and an (n- or i-)propanesulfonyl group), and $C_{6-10}$ arylsulfonyl groups (e.g., a benzenesulfonyl group, a (o-, m-, or p-)toluenesulfonyl group, and a (1- or 2-)naphthalenesulfonyl group). As a result of substitution or protection, the carboxyl groups, for example, that are contained in the residues may be converted to $C_{1-6}$ alkoxycarbonyl groups; the hydroxy groups in the residues may be converted to $C_{1-6}$ alkoxy groups or $C_{1-6}$ alkylcarbonyloxy groups; and the amino groups in the residues may be converted to $C_{1-6}$ alkylamino groups, di-$C_{1-6}$ alkylamino groups, $C_{1-6}$ alkylcarbonylamino groups, or N—$C_{1-6}$ alkyl-$C_{1-6}$ alkylcarbonylamino groups. In addition, the carboxyl groups contained in the residues are optionally converted to an amide group optionally substituted by one or two $C_{1-6}$ alkyl groups. When nitrogen-containing heterocycles such as an indole ring and an imidzole ring are contained in the residues, the nitrogen atoms on the rings may each independently be protected by a $C_{1-6}$ alkyl group or a $C_{1-6}$ alkylcarbonyl group. When a guanidino group is contained in the residue, the nitrogen atom present in it may also be protected by a $C_{1-6}$ alkyl group or a $C_{1-6}$ alkylcarbonyl group. Other protective groups for the nitrogen atom are not particularly limited, but may also be selected from commonly used groups such as the above-described alkoxycarbonyl, formyl, $C_{1-6}$ alkylsulfonyl, and $C_{1-6}$ arylsulfonyl groups. When a thiol group is contained in the residue, it may be protected by a $C_{1-6}$ alkyl group or a $C_{1-6}$ alkylcarbonyl group. In addition, the amide bond contained in the peptide chain may also be substituted by a $C_{1-6}$ alkyl group and/or a $C_{1-6}$ alkylcarbonyl group so that it may be converted, for example, to —CON($C_{1-6}$ alkyl)-.

The amino acid sequence composing the peptide chain is not particularly limited but may be exemplified by the following. In this regard, if there is an in vivo protease as the target and the amino acid sequence for recognition of its substrate is known, an amino acid sequence containing the recognition site and/or cleavage site may also be used.

Peptide chains consisting of one amino acid: Ala, Arg, Asn, Asp, Cys, Gln, Glu, Gly, His, Ile, Leu, Lys, Met, Phe, Pro, Ser, Thr, Trp, Tyr, Val, and the like, with Phe, Tyr, Ile, and Glu being preferred.

Peptide chains consisting of two amino acids: PhePhe, PheGly, PheLeu, TyrPhe, TrpPhe, PheTrp, PheTyr, GlyPhe, GlyGly, and the like, with PhePhe and PheGly being preferred.

Peptide chains consisting of three amino acids: PheGlyGly, PheLeuGly, PhePheGly, AsnPhePhe, GlyPhePhe, LeuPhePhe, LeuAlaLeu, AlaValAla, GlyAlaPhe, GlyPheAla, GlyIleAla, GlyIlePhe, GlyLeuAla, GlyValAla, GlyValPhe, GlyGlyGly, and the like, with AsnPhePhe being preferred.

Peptide chains consisting of four amino acids: GlyPheLeuGly, GlyPhePheLeu, GlyPhePheAla, GlyPheTyrAla, GlyPheGlyPhe, GlyPheGlyGly, GlyGlyPheGly, GlyGlyPheTyr, GlyGlyGlyGly, LeuAlaLeuAla, AlaLeuAlaLeu, AlaGlyValPhe, GluAsnPhePhe, and the like, with GlyPheLeuGly being preferred.

The linker according to the present invention may have a structure represented by, for example, formula (X) above, where $Q_1$ forms, together with —NH— binding thereto, a peptide chain consisting of 1 to 8 of the amino acids as described above. In addition, $Q_2$ is $C_{2-20}$ alkylene which optionally has 1 to 5 oxygen atoms inserted thereinto or which is optionally substituted by a carboxyl group or a $C_{1-6}$ alkoxycarbonyl group. Specific examples of $Q_2$ include an ethane-1,2-diyl group, propane-1,3-diyl group, butane-1,4-diyl group, pentane-1,5-diyl group, hexane-1,6-diyl group, heptane-1,7-diyl group, octane-1,8-diyl group, nonane-1,9-diyl group, decane-1,10-diyl group, 2-methylpropane-1,3-diyl group, 2-methylbutane-1,4-diyl group, 3-methylbutane-1,4-diyl group, 3-methylpentane-1,5-diyl group, 3-ethylpentane-1,5-diyl group, 2-methylhexane-1,6-diyl group, 3-methylhexane-1,6-diyl group, 4-methylheptane-1,7-diyl group, 3-oxapentane-1,5-diyl group, 3-oxahexane-1,6-diyl group, 4-oxahexane-1,6-diyl group, 3-oxaheptane-1,7-diyl group, 4-oxaheptane-1,7-diyl group, 4-oxaoctane-1,8-diyl group, 3,6-dioxaoctane-1,8-diyl group, 3,6-dioxanonane-1,9-diyl group, 3,6-dioxa-4-methylnonane-1,9-diyl group, 4,7-dioxadecane-1,10-diyl group, 4,9-dioxadodecane-1,12-diyl group, and 4,7,10-trioxatridecane-1,13-diyl group. Preferred examples include an ethane-1,2-diyl group, pentane-1,5-diyl group, 3-oxapentane-1,5-diyl group, 3,6-dioxaoctane-1,8-diyl group, 4,7-dioxadecane-1,10-diyl group, 4,9-dioxadodecane-1,12-diyl group, and 4,7,10-trioxatridecane-1,13-diyl group.

The HA-MTX conjugate to be used in the composition of the present invention is not particularly limited in terms of the mode in which MTX is conjugated with the linker. Typically, however, the linker containing a peptide chain is bound to:
1) the carboxyl group at the α-position of MTX;
2) the carboxyl group at the γ-position of MTX; or
3) the amino group of MTX.

If desired, a plurality of these linking modes may coexist (for example, a conjugate with the linker bound to the carboxyl group at the α-position of MTX and a conjugate with the linker bound to the carboxyl group at the γ-position of MTX may coexist). However, from the viewpoint of affinity to protease and considerations for synthesis, the linker containing a peptide chain is preferably bound to the carboxyl group at the α-position of MTX and/or the carboxyl group at the γ-position of MTX, with the linker bound to the carboxyl group at the α-position of MTX being more preferred.

Among the HA-MTX conjugates to be used in the composition of the present invention, those which have a particularly preferred linker containing a peptide chain and a particularly preferred binding mode are those in which the linker containing a peptide chain is such that a diamino compound is present at the end of the peptide chain which consists of α-amino acids, with the N-terminal of the peptide chain being bound to the carboxyl group at the α-position of MTX through acid amide bonding and the C-terminal of the peptide chain being bound to a carboxyl group in HA through acid amide bonding via the diamino compound.

The methotrexate (MTX) moiety in the HA-MTX conjugate of the present invention may be converted to a prodrug form by known methods aside from the modification by the linker.

As used herein, the $C_{1-6}$ alkyl group refers to a straight-chain or branched alkyl group of 1-6 carbon atoms and examples include a methyl group, an ethyl group, a n-propyl group, an i-propyl group, a n-butyl group, a s-butyl group, an i-butyl group, a t-butyl group, a n-pentyl group, a 3-methylbutyl group, a 2-methylbutyl group, a 1-methylbutyl group, a 1-ethylpropyl group, and a n-hexyl group.

As used herein, the $C_{1-6}$ alkylcarbonyl refers to a straight-chain or branched alkylcarbonyl group of 1-6 carbon atoms and examples include an acetyl group, a propionyl group, a 2-methylpropionyl group, a 2,2-dimethylpropionyl group and others that have the already defined alkyl group as the alkyl part.

As used herein, the $C_{1-6}$ alkoxy refers to a straight-chain or branched alkoxy group of 1-6 carbon atoms and examples include a methoxy group, an ethoxy group, a n-propoxy group and others that have the already defined alkyl group as the alkyl part.

As used herein, the $C_{1-6}$ alkylamino refers to a straight-chain or branched alkylamino group of 1-6 carbon atoms and examples include a methylamino group, an ethylamino group, a n-propylamino group and others that have the already defined alkyl group as the alkyl part.

As used herein, the di-$C_{1-6}$ alkylamino refers to a straight-chain or branched dialkylamino group of 1-6 carbon atoms and examples include a dimethylamino group, an ethylmethylamino group, a diethylamino group, an ethyl-n-propylamino group and others that have as the alkyl part the already defined alkyl groups which may be the same or different.

As used herein, the di-$C_{2-20}$ alkylene refers to a straight-chain or branched alkylene group of 2-20 carbon atoms and examples include an ethylene group, a propylene group, a butylene group, an octylene group, a decalene group, etc.

As used herein, the $C_{1-6}$ alkoxycarbonyl group refers to a straight-chain or branched alkoxycarbonyl group of 1-6 carbon atoms and examples include a methoxycarbonyl group, an ethoxycarbonyl group, a n-propoxycarbonyl group and others that have the already defined alkyl group as the alkyl part.

As used herein, the $C_{1-6}$ alkylsulfonyl group refers to a straight-chain or branched alkylsulfonyl group of 1-6 carbon atoms and examples include a methanesulfonyl group, an ethanesulfonyl group, a n-propanesulfonyl group and others that have the already defined alkyl group as the alkyl part.

As used herein, the acylation includes $C_{1-6}$ alkylcarbonylation and benzoylation, with the introduced benzoyl group being optionally substituted by a $C_{1-6}$ alkyl, a halogen atom, a $C_{1-6}$ alkoxy, etc.

The percent conjugation of MTX in the HA-MTX conjugate of the present invention is preferably in such a range that the pharmaceutical efficacy is exhibited with no concern about side effects. As used herein, the percent conjugation of MTX is calculated by the following equation:

$$(\text{Percent conjugation of } MTX\ (\%)) = \frac{(\text{Number of } MTX \text{ moieties conjugated in a molecule})}{(\text{Number of glucuronic acid moieties in a molecule})} \times 100$$

The percent conjugation of MTX is not particularly limited but in view of the development of the pharmaceutical efficacy, it is preferably 0.5% or higher, more preferably 1.0% or higher. On the other hand, the percent conjugation of MTX is preferably smaller than 10% in order to localize the action of MTX in the administration region and to reduce the systemic side effects of MTX. In addition, considering that the HA-MTX conjugate of the present invention has high molecular weight and also considering the possibility that if it has high percent conjugation of MTX, insolubilization might occur to cause some inconvenience in synthesis, the percent conjugation of MTX is preferably 0.5% or higher but smaller than 4.5%, with the range of from 1.0% or higher to smaller than 4.5% being particularly preferred.

The HA-MTX conjugate of the present invention may also be present as a salt and considering its uses, the salt is preferably a pharmaceutically acceptable salt. Examples include sodium salt, potassium salt, calcium salt, aluminum salt, zinc salt, iron salt, ammonium salt, tetrabutylammonium salt, etc.

To synthesize the HA-MTX conjugate, the methods described in WO05/85294 may be used as appropriate. Stated briefly, HA, the linker containing a peptide chain, and MTX may be conjugated in an appropriate order to produce the HA-MTX conjugate. The conjugating reactions involved can be performed using solvents, condensing agents, and optional reaction promoting additives that are employed in ordinary acid amide linking reactions. Reaction conditions such as solvents, condensing agents and temperature need be chosen as appropriate in consideration of the disclosures in WO05/85294 and the common technical knowledge in the field of organic chemistry.

Photostabilizer

The term "photostabilizer" as used herein refers to a substance having either a quenching effect to absorb energy from a molecule in an excited state caused by irradiation with light, or a radical scavenging effect capable of scavenging radicals, or both of these effects.

A preferred quencher is one that has the ability to suppress the generation of fluorescence that is emitted from the HA-MTX conjugate upon excitation by irradiation with light of 320-430 nm (this ability may be called a quenching effect).

Examples of the photostabilizer having the quenching effect and/or the radical scavenging effect that can advantageously be used in the present invention include the following compounds (a) to (c).

(a) Sulfur-Containing Inorganic Acids or Organic Acids and Salts Thereof

This class of compounds includes, for example, sodium thiosulfate, thioglycolic acid, ammonium thioglycolate, sodium thioglycolate, potassium thioglycolate, ethyl thioglycolate, thiomalic acid, ammonium thiomalate, sodium thiomalate, potassium thiomalate, mercaptopropionic acid, ammonium mercaptopropionate, sodium mercaptopropionate, and potassium mercaptopropionate.

Preferred compounds are thiosulfuric acid, sodium thiosulfate, thioglycolic acid, ammonium thioglycolate, sodium thioglycolate, potassium thioglycolate, and ethyl thioglycolate.

Particularly preferred compounds are thiosulfuric acid, sodium thiosulfate, and sodium thioglycolate.

(b) Aromatic Amino Acid Derivatives and Salts Thereof

This class of compounds includes, for example, N-acetyltryptophan, tryptophan, tryptophan methyl ester, tryptophan ethyl ester, tyrosine, and phenylalanine, as well as salts thereof.

Particularly preferred compounds are N-acetyltryptophan and tryptophan.

A particularly preferred compound is N-acetyltryptophan.

Salts of these amino acid derivatives are not particularly limited and include, for example, acid addition salts such as hydrochlorides, nitrates, sulfates, and phosphates; and base addition salts such as sodium salt, potassium salt, calcium salt, aluminum salt, zinc salt, iron salt, ammonium salt, and tetrabutylammonium salt.

(c) Hydroxybenzoic Acids and Salts Thereof

This class of compounds includes, for example, salicylic acid, sodium salicylate, methyl salicylate, ethyl salicylate, phenyl salicylate, benzyl salicylate, isoamyl salicylate, methyl p-hydroxybenzoate (methyl paraben), ethyl p-hydroxybenzoate, propyl p-hydroxybenzoate, n-butyl p-hydroxybenzoate, isobutyl p-hydroxybenzoate, 4-hydroxybenzoic acid, sodium 4-hydroxybenzoate, 3-hydroxybenzoic acid, and sodium 3-hydroxybenzoate.

Preferred compounds are salicylic acid, sodium salicylate, methyl p-hydroxybenzoate, and propyl p-hydroxybenzoate.

Particularly preferred compounds are salicylic acid, sodium salicylate, and methyl p-hydroxybenzoate.

Although not wishing to be bound by theory, the photostabilizer of the present invention is believed to exhibit its efficacy in the following manner.

To begin with, the first reaction that takes place upon irradiation with light is described by referring to FIG. 1. The MTX moiety of the HA-MTX conjugate irradiated with light becomes excited. In this case, fluorescence emission is believed to take place in the process of electronic transition from the excited singlet state to the ground state. Compound (a) having a pteridine ring is easy to be eliminated from the MTX moiety in the excited state, and after it is eliminated, the remaining moiety of the conjugate, i.e., pteridine ring free MTX-linker-HA designated as (b) that contains a 2-(4-aminobenzoylamino)-4-carboxylbutylcarbonyl group, is formed (reaction A). Two such remaining moieties (b) combine to form an azo dimer (reaction B), which eventually is believed to result in the crosslinking of two hyaluronic acid molecules via the azo dimer.

As a matter of fact, in view of a substantial agreement between the region of the excitation wavelength where the HA-MTX conjugate emits fluorescence and the wavelength region of light that causes gelation of the conjugate (Example 1), and also considering that the irradiated HA-MTX conjugate contains the azo dimer formed as the result of elimination of the pteridine ring from MTX (Examples 2 and 3), the fluorescing and gelation of the HA-MTX conjugate are believed to be closely related. The photostabilizer to be used in the present invention has a strong quenching action (the ability to absorb energy from a molecule in an excited state, whereby fluorescing is relatively suppressed), and even when the HA-MTX conjugate was irradiated with light at an excitation wavelength which could enable the conjugate to emit fluorescence, the conjugate was suppressed from fluorescing in the presence of the photostabilizer (Example 4). Consequently, the elimination of the pteridine ring and the formation of the azo dimer that would otherwise take place subsequent to the excitation are suppressed, which may eventually lead to suppressed gelation.

There is one more reaction that is believed to take place upon irradiation with light. That is a decrease in the molecular weight of the HA-MTX conjugate. This reaction is believed to take place if the molecule of the HA polymer is cleaved when it is directly acted upon by the MTX moiety that has becomes excited upon irradiation with light or a compound having the pteridine ring eliminated from the MTX moiety, or when it is indirectly acted upon by radical species generated by a photochemical reaction that involves the compound having the pteridine ring. The photostabilizer of the present invention is believed to suppress the decrease in the molecular weight of the HA-MTX conjugate either by suppressing the elimination of the pteridine ring or the subsequently occurring photochemical reaction itself on account of the strong quenching action on the excited MTX moiety, or by scavenging the radical species generated by the photochemical reaction.

Pharmaceutical Composition of the Present Invention

Like the HA-MTX conjugate containing pharmaceutical composition that is described in WO05/85294, the pharmaceutical composition of the present invention that contains both the HA-MTX conjugate and the photostabilizer is also effective for the treatment of joint diseases.

As used herein, the "joint diseases" refers specifically to diseases such as articular cartilage defect, osteoarthritis (including a primary disease with no evident cause, and a secondary disease with a recognizable causative disease), shoulder periarthritis, rheumatoid arthritis, reactive arthritis, viral arthritis, suppurative arthritis, tuberculous arthritis, and neuroarthropathy, further including joint pains in these diseases (for example, knee joint pain in rheumatoid arthritis). As used herein, the "therapeutic drug for joint diseases" includes not only drugs used for treating the above-mentioned joint diseases but also drugs used for preventing them, suppressing the progression of the pathologic condition (preventing exacerbation or maintaining the current condition), and for other purposes.

The HA-MTX conjugate may be used as a pharmaceutical composition which contains it in an effective amount, with pharmaceutically acceptable ingredients such as carrier, excipient, disintegrant, lubricant, binder, perfume, and colorant being added as appropriate. The pharmaceutical composition containing the HA-MTX conjugate of the present invention as the active ingredient is preferably used as a therapeutic drug for joint diseases and it is particularly preferred to use this composition as a preparation for topical administration into the joint.

The method of formulating the pharmaceutical composition of the present invention as a preparation (for example, as a therapeutic drug for joint diseases) is not particularly limited but in one example, the HA-MTX conjugate and the photostabilizer may be dissolved in physiological saline, phosphate physiological saline or the like at desired concentrations to formulate a solution for injection; alternatively, they may be formulated as a powder for injection that is dissolved just before use. In these cases, an acid or base may optionally be added to adjust the pH of the solution to a desired value. To adjust the salt concentration of solution to a desired level, an inorganic salt may be added, as selected from among monovalent metal salts such as sodium salt and potassium salt, and divalent metal salts such as magnesium salt, calcium salt, and manganese salt. If desired, a stabilizer and the like may also be added. The thus prepared solution of the HA-MTX conjugate may be distributed on the market in such a form that it is preliminarily charged in an injection syringe such as a disposable cylinder.

When the composition of the present invention is to be administered as a therapeutic drug for joint diseases containing the HA-MTX conjugate as the active ingredient, the composition containing the HA-MTX conjugate at a concentration in solution of 0.01% to 10% (w/v), preferably 0.1% to 2.0% (w/v), more preferably 0.5% to 1.5% (w/v) may be administered to the patient at a dose of 1 to 3 mL per time. However, the dose may be adjusted to an optimum level as appropriate for the physician's instructions, the patient to be treated, the type and severity of the disease, the molecular weight of the HA-MTX conjugate, and other factors.

If the pharmaceutical composition of the present invention is a solution (say, a solution for injection), the photostabilizer is present in the solution at a concentration in the range of 0.01 to 30% (w/v), preferably 0.1 to 20% (w/v), more preferably 0.5 to 15% (w/v) ("% (w/v)" represents the number of grams of the substance of interest that is dissolved in 100 ml of the solution; 30% (w/v), for example, means that 30 g of the photostabilizer is dissolved in 100 ml of the solution.) In the case where the composition is a powder that is to be dissolved just before use (say, a powder for injection), the photostabilizer is contained in such a way that a solution prepared by dissolving the powder in an amount that is specified in the instructions for the product contains the photostabilizer at a concentration in the range of 0.01 to 30% (w/v), preferably 0.1 to 20% (w/v), more preferably 0.5 to 15% (w/v).

Packaging Material

In the present invention, the pharmaceutical composition of the present invention may be packaged with a material that blocks light having a specified wavelength, and this is preferred since this further improves its stability to irradiation with light. A film laminated with a substance such as aluminum that provides 100% blocking of light transmission may be used, but considering the convenience in actual medical settings, the use of a package through which the contents can be identified provides higher commercial value and hence is preferred over completely blocking the transmission of light. A packaging material that retains light transmission to an extent that enables the contents of the package to be identified through it, and which contributes to stabilizing the pharmaceutical composition of the present invention is characterized by blocking light of wavelengths in a specified range that can be harmful to stability, or reducing the transmittance of light having wavelengths in that range; and using such packaging material not only improves the stability of the packaged pharmaceutical composition during irradiation with light, but it is also preferred from the viewpoint of commercial value. A packaging material that at least blocks light having a wavelength of 320 nm to 430 nm is preferably used, and more preferably, a packaging material that at least blocks light having a wavelength of 540 nm or less can advantageously be used. Light of wavelengths outside the stated ranges may or may not be blocked, but from the viewpoint of assuring that the contents of the package can be identified from the outside, the packaging material is preferably characterized in that it does not block or attenuate light having at least part of the wavelengths not included within the stated ranges, preferably light at all wavelengths outside the stated ranges, more preferably light with wavelengths of the visible region (380-780 nm) but not included within the stated ranges.

It should be noted that packaging materials such as aluminum-laminated films that block light of all wavelengths including those within the above-specified ranges may be used in combination with the packaging material that does not block light other than the light having wavelengths in the above-specified ranges. For example, individual packages of the product that use the packaging material that does not block light other than the light having wavelengths in the above-specified ranges so that the contents can be identified until just before use on medical settings may be packed in several units into a larger box that is covered with a packaging material such as aluminum-laminated film that blocks light of all wavelengths including those within the above-specified ranges.

As used herein, a certain substance that has a "light shielding" action or the ability to "block light" is supposed to have a light transmittance of 10% or less. Light transmittance may be measured by any method that is known to the skilled artisan and it may be measured with a spectrophotometer as described in Example 5 to be set forth later. From the viewpoint of preventing gelation and a decrease in the molecular weight of the HA-MTX conjugate, the transmittance of light with which the HA-MTX conjugate is to be irradiated is desirably low. Preferably, light within the range where gelation and a decrease in the molecular weight of the HA-MTX conjugate in the actual environment of use, namely, in the range of 320 nm to 430 nm, preferably 540 nm or less, is "shielded" or "blocked."

Useful packaging materials include plastic films, e.g., polyester films, polyvinylidene fluoride (PVDF) films, or glass, colored with dyes or pigments such as titanium oxide and carbon black that are capable of absorbing light having the above-noted wavelengths.

Packaging is done by using containers composed of packaging materials having these features or covering the outside of containers with such packaging materials. Cases that may be assumed include constituting syringe or vial containers of the packaging materials having those features or packaging ordinary syringes or vials with the packaging materials having those features.

In the present invention, not all parts of the packaging materials used on pharmaceuticals need be capable of blocking light. Preferably, however, the greater part, more preferably all, of the packaging materials for pharmaceuticals are composed of packaging materials that at least block light of wavelengths in the above-specified ranges.

If the packaging materials such as the light-shielding film described above are used, adequate stability can be secured even if a smaller amount of the photostabilizer is used. Specifically, the amount of the photostabilizer to be used can be reduced to about 0.01-2% (w/v), preferably about 0.05-1% w/v), of the composition.

EXAMPLES

The present invention is described in greater detail by referring to the following Examples, which are by no means intended to limit the scope of the present invention.

Production 1

Production of HA-MTX Conjugate

In accordance with a modification of the method described in Example 2-1 of WO05/85294, a sodium salt of hyaluronic acid was conjugated to a linker-bound methotrexate(2-[N—[N—[N-[4-[[2,4-diamino-6-pteridinyl]methyl]methylamino]benzoyl]-α-(O5-methylglutamyl)]phenylalanyl)phenylalanylamino]ethylamine: MTX-α-PhePhe-NH—$C_2H_4$—$NH_2$) to produce a HA-MTX conjugate (MTX-α-PhePhe-NH$C_2H_4$NH-HA, DK-226). The molecular weight of the conjugate was determined by a gel filtration chromatographic technique using hyaluronic acid as a standard substance. For gel filtration chromatography, an apparatus equipped with OHPakSB-806HQ (Shodex) as a column and an RI detector RI-71 (Shodex) and UV detector 875-UV (JASCO, detection wavelength: 304 nm) as detectors was used and analysis was conducted under the following conditions: eluent, 50 mM sodium phosphate aqueous solution (pH 6.0); elution rate, 0.6 mL/min; column temperature, 40° C.

As standard substances, hyaluronic acid samples were prepared in varying molecular weights and their accurate values were calculated by the limiting viscosity method before it was used. By the above-described gel filtration chromatography, the elution times of the conjugate under consideration were determined and its molecular weight was determined from the relationship between the elution times and the molecular weights of the standard substances. The conjugate was found to have a molecular weight of about 2,070,000. The percent conjugation of MTX in the conjugate was 2.2% when calculated by measuring the ultraviolet absorption (259 nm). The HA-MTX conjugate was dried and stored as a powder until it was subjected to the following experiment.

Example 1

This experiment was conducted to verify the gelation of the HA-MTX conjugate upon irradiation with light at specified wavelengths as well as the relationship between the gelation and fluorescing.

The HA-MTX conjugate obtained in Production 1 was dissolved in 0.9% NaCl containing 2 mM phosphate buffer (pH 7.3) to give a concentration of 9.9 mg/ml in terms of HA and the solution was irradiated with light at varying wavelengths (260 nm, 310 nm, 360 nm, and 405 nm) using a fluorescence detector for liquid chromatography (product of Hitachi, Ltd.; fluorescence detector of model F1050) to observe the gelation and fluorescing of the conjugate. To evaluate the gelation, the surface of the sample solution was pierced with a spatula and visually checked for the formation of an interface as the result of gelation. To observe fluorescing, the sample was irradiated with exciting light and the state of light emission from the sample was observed by direct visual checking before and after the irradiation; the result was rated "+" when strong emission was observed after the irradiation but rated "−" when the emission after the irradiation was not different from the emission before the irradiation. The results are shown in Table 1.

TABLE 1

| Wavelength | Gelation | Fluorescence |
|---|---|---|
| 405 nm | gelled in 1 h | + |
| 360 nm | gelled in 1 h | + |
| 310 nm | gelled in 6 h | − |
| 260 nm | did not gel in 24 h | − |

As Table 1 shows, when the HA-MTX conjugate was irradiated with specified wavelengths of light, strong fluorescence was observed visually at 360 nm and 405 nm. At these wavelengths, the conjugate gelled in an hour. Even the sample irradiated with light of 310 nm gelled in 6 hours. On the other hand, the sample irradiated with light of 260 nm did not gel even after the passage of 24 hours.

The foregoing results revealed that light having wavelengths in a certain range caused the HA-MTX conjugate to gel and fluoresce. The wavelength range causing gelation is presumably such that the limit on the short wavelength side is longer than 260 nm but shorter than 310 nm whereas the limit on the long wavelength side is longer than 405 nm. In particular, the wavelength range causing gelation within a short time is presumably such that the limit on the short wavelength side is longer than 310 nm but shorter than 360 nm whereas the limit on the long wavelength side is longer than 405 nm. In addition, as will be explained in Example 4, the excitation wavelength range for the HA-MTX conjugate was that of 320-430 nm including 360 nm and 405 nm at which intense fluorescence and quick gelation were visually observed (see Table 1); this suggests that the gelation and fluorescing of the HA-MTX conjugate is closely related to the excitation wavelength for the HA-MTX conjugate.

Example 2

Example 2 and Example 3 to be described later were conducted to study the mechanisms of the reactions that would take place in the HA-MTX conjugate upon irradiation with light.

Method

The HA chains in the HA-MTX conjugate irradiated with light were cleaved with a hyaluronic acid decomposing enzyme and the resulting product was analyzed to estimate its structure.

Specifically, a HA-MTX conjugate (DK-226: MTX-α-PhePhe-NHC$_2$H$_4$NH-HA, percent conjugation of MTX in the conjugate=2.1%; molecular weight of the conjugate=2,060,000) was prepared in accordance with a modification of the method described in Example 2-1 of WO05/85294; using this conjugate, the following procedure was taken.

The conjugate was dissolved in 0.9% NaCl containing 2 mM phosphate buffer (pH 7.3) to prepare a solution whose concentration was 10.5 mg/ml in terms of HA. A portion (1 ml) of the conjugate solution was sampled and irradiated with light (5000 Lux×24 hr) from a fluorescent lamp for use in a photostability test (TOSHIBA FL20S•D-EDL-D65); thereafter, 50 mM phosphate buffer (pH 6.0) containing Chondoroitinase ACII (SEIKAGAKU CORPORATION) as prepared at a concentration of 5 U/ml was added in an amount of 1 ml and cleavage of the HA chains was performed at 37° C. for 3 days (test sample). In a separate run, 1 ml of the conjugate solution was used without being irradiated with light, and to this solution, 50 mM phosphate buffer (pH 6.0) containing the above-identified enzyme as prepared at a concentration of 0.5 U/ml was added in an amount of 1 ml, and cleavage of the HA chains was performed at 37° C. for one day (control).

The thus obtained test sample and control were analyzed by gel filtration chromatography and reverse-phase liquid chromatography under the following conditions. The apparatus used in each analysis was SMART system (product of Pharmacia), with the UV detector employing wavelengths of 205 nm, 220 nm, and 310 nm.

In gel filtration chromatography, the enzymatically digested solution was diluted 50-folds with 0.1% TFA containing 30% CH$_3$CN and passed through a 0.45-μm filter; 20 μl of the filtrate was used in analysis. Superdex Peptide PC 3.2/23 was used as the column and 0.1% TFA containing 30% CH$_3$CN was used as the eluate; analysis was performed at an elution rate of 100 μl/min.

In reverse-phase chromatography, the enzymatically digested solution was diluted 50-folds with 0.1% TFA containing 30% CH$_3$CN and passed through a 0.45-μm filter; 20 μl of the filtrate was used in analysis. The column was μRPC C2/C18 PC 3.2/3 and the eluate system employed a gradient in composition consisting of eluate A (0.1% TFA aqueous solution) and eluate B (0.1% TFA containing CH$_3$CN solution), with analysis being conducted at an elution rate of 200 μl/min. The gradient satisfied the following conditions: the percent ratio (v/v) of eluate B in the eluate system (a mixture of eluates A and B) was maintained at 0% for 0-5 min after the start of analysis, increased linearly from 0% to 50% at a rate of 2% per minute in the period of 5-30 min, maintained at 100% for 30-35 min, and then maintained at 0% for 35-40 min.

Results

Figure 2A:
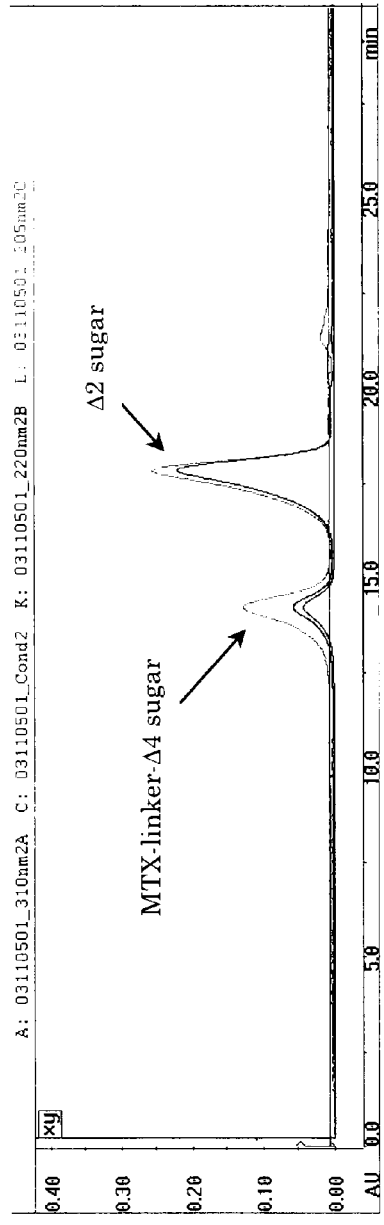
FIG. 2A shows HPLC charts for the HA-MTX conjugate that was not irradiated with light but was digested with an enzyme.
Figure 2A:
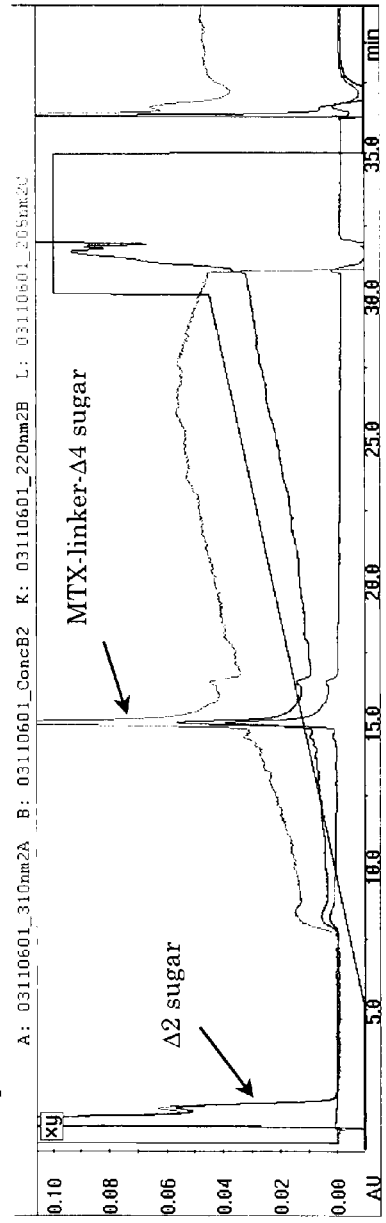
Figure 2B:
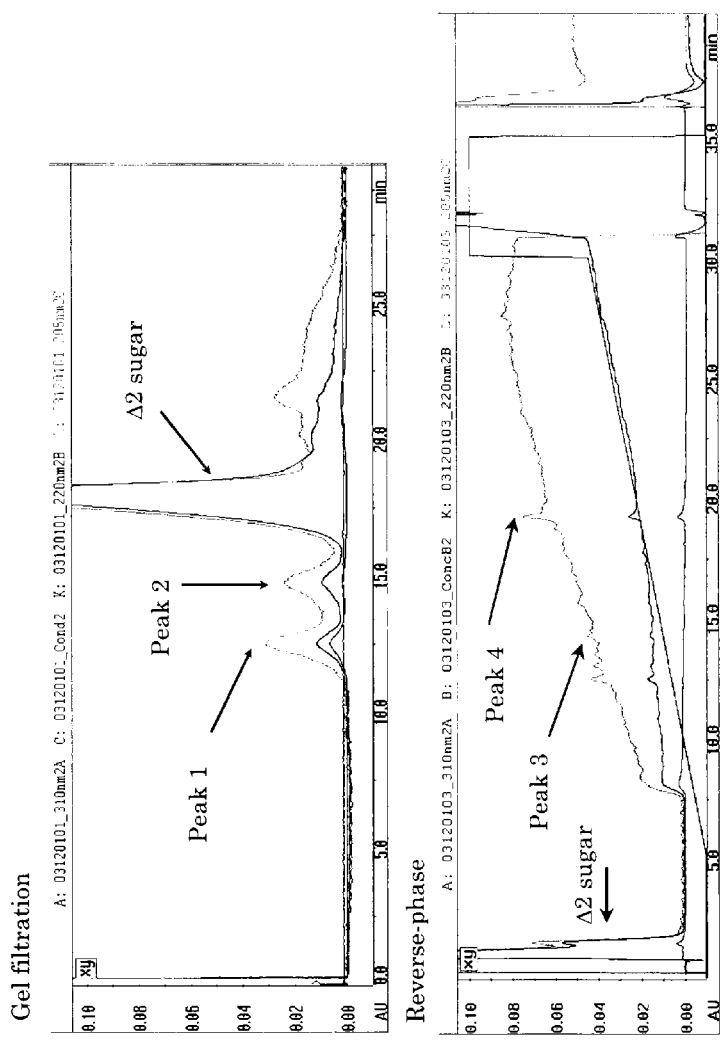
FIG. 2B shows HPLC charts for the HA-MTX conjugate that was digested with an enzyme after irradiation with light.

As the result of performing gel filtration or reverse-phase chromatographic analysis on the control, two peaks were recognized that might be attributed to two sugar units (which may hereinafter be referred to as "Δ2 sugar") and a MTX-linker molecule to which four sugar units were bound (which may hereinafter be referred to as "MTX-linker-Δ4 sugar") (FIG. 2A). Subsequently, the same analysis was conducted on the test sample and, as the result, new peaks 1, 2, 3 and 4 were recognized that differed from both Δ2 sugar and MTX-linker-Δ4 sugar (FIG. 2B). Compounds corresponding to these new peaks were isolated and analyzed as described in Example 3.

Example 3

Figure 3:
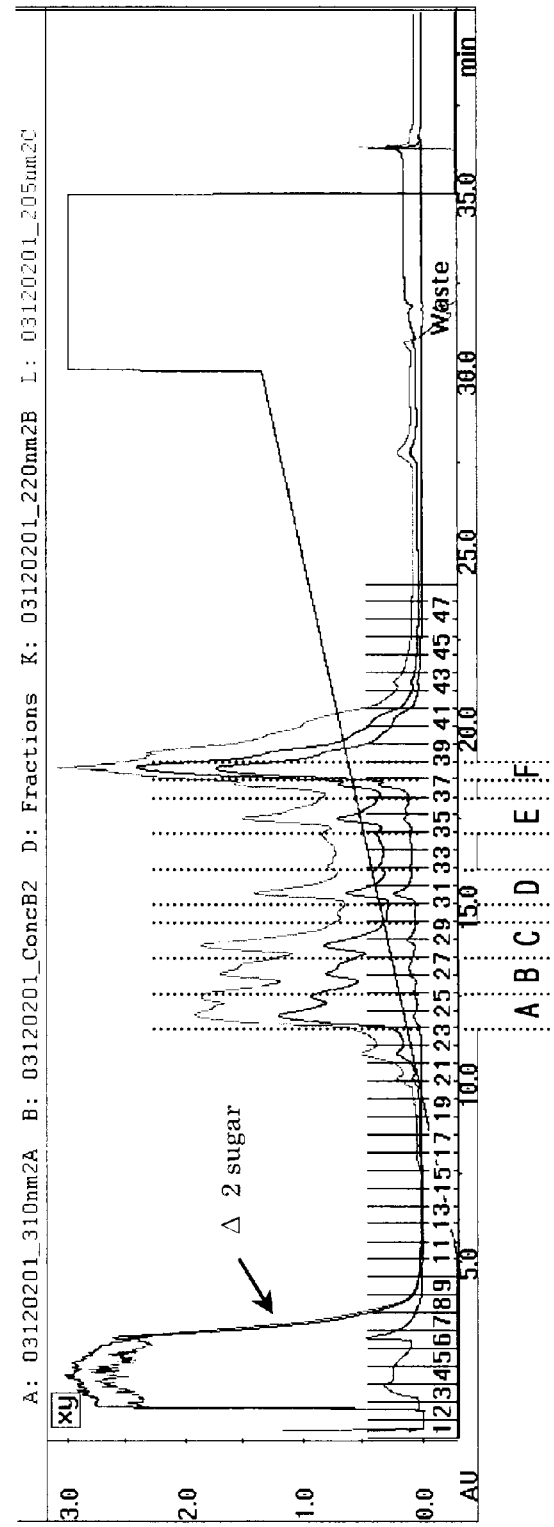
FIG. 3 is a reverse-phase preparative HPLC chart for the HA-MTX conjugate that was digested with an enzyme after irradiation with light.

A test sample prepared by the method described in Example 2 was subjected to preparative liquid chromatography using a reverse-phase column. The chromatograph obtained is shown in FIG. 3.

The analysis conditions were as follows.

As a test sample for preparative chromatography, the enzymatically digested solution in an undiluted form was passed through a 0.45-μm filter and 200 μl of the filtrate was used in analysis. The apparatus used was SMART system (product of Pharmacia), with the UV detector employing wavelengths of 205 nm, 220 nm, and 310 nm. The column was μRPC C2/C18 PC 3.2/3 and the eluate system employed a gradient in composition consisting of eluate A (0.1% TFA aqueous solution) and eluate B (0.1% TFA containing CH₃CN solution), with analysis being conducted at an elution rate of 200 μl/min.

The gradient satisfied the following conditions: the percent ratio (v/v) of eluate B in the eluate system (a mixture of eluates A and B) was maintained at 0% for 0-5 min after the start of analysis, increased linearly from 0% to 50% at a rate of 2% per minute in the period of 5-30 min, maintained at 100% for 30-35 min, and then maintained at 0% for 35-40 min.

The eluate for the period immediately after the start of analysis up to 24 min was sampled in 100-μl portions into test tubes; fractions A-F (retention time: 11.5-14.5 min (A-C); 15.0-16.0 min (D); 17.0-18.0 min (E), and 18.5-19.0 min (F)) shown in FIG. 3 were sampled and each subjected to LC/MS analysis. The results are shown in Table 2.

TABLE 2

MS analysis of Acquired Fractions (LC/MS; ionization mode, ESI (+))

| Frac. | Main m/z (auxiliary m/z) | Putative structure |
|---|---|---|
| A-C | 1365.6 (1273.5, etc.) | [pteridine ring free MTX-linker-Δ4 sugar] (Formula a) |
| D | 1531.1 | [MTX-linker-Δ4 sugar + H]⁺ |
|  | 1553.5 (1598.2, etc.) | [MTX-linker-Δ4 sugar + Na]⁺ |
| E | 1363.7 (1374.7, etc.) | [pteridine ring free MTX-linker's azo dimer + 2Na]²⁺ |
| F* | 1363.7 | [pteridine ring free MTX-linker's azo dimer + 2Na]²⁺ |
|  | 1720.5 |  |
|  | 1942.6 (1924.5, etc.) | [pteridine ring free MTX-linker-Δ2 sugar's azo dimer-H₂O + H]⁺ |

F* has the same UV absorption maximum as the azo dimer resulting from the photolysis product of MTX.

The main m/z values of the components contained in fractions A to C as indicated in Table 2 are presumably assigned to the structure represented by the following formula a:

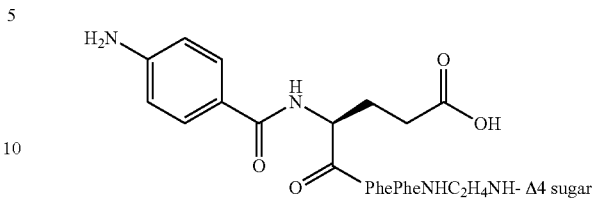

In other words, it was presumed that a compound with the pteridine ring being eliminated from the MTX-linker-Δ4 sugar structure was generated.

As Table 2 also shows, the m/z values detected by mass analysis of fractions E and F correspond to sodium added ions of the azo dimer that was generated upon elimination of the pteridine ring from MTX. When the UV absorption of fraction F was measured with a spectrophotometer (product of Hitachi, Ltd.: double-beam spectrophotometer of model U-2000; scan speed, 400 nm/min), fraction F had the same UV absorption maximum (ca. 330 nm) as the azo dimer isolated from the photolysis product of MTX per se (see the data for compound II in Phtochemistry and Photobiology, vol. 44, No. 2, pp. 231-233, 1986; C. chahide et al.) These data suggest the presence of those dimers in fractions E and F.

Figure 4:
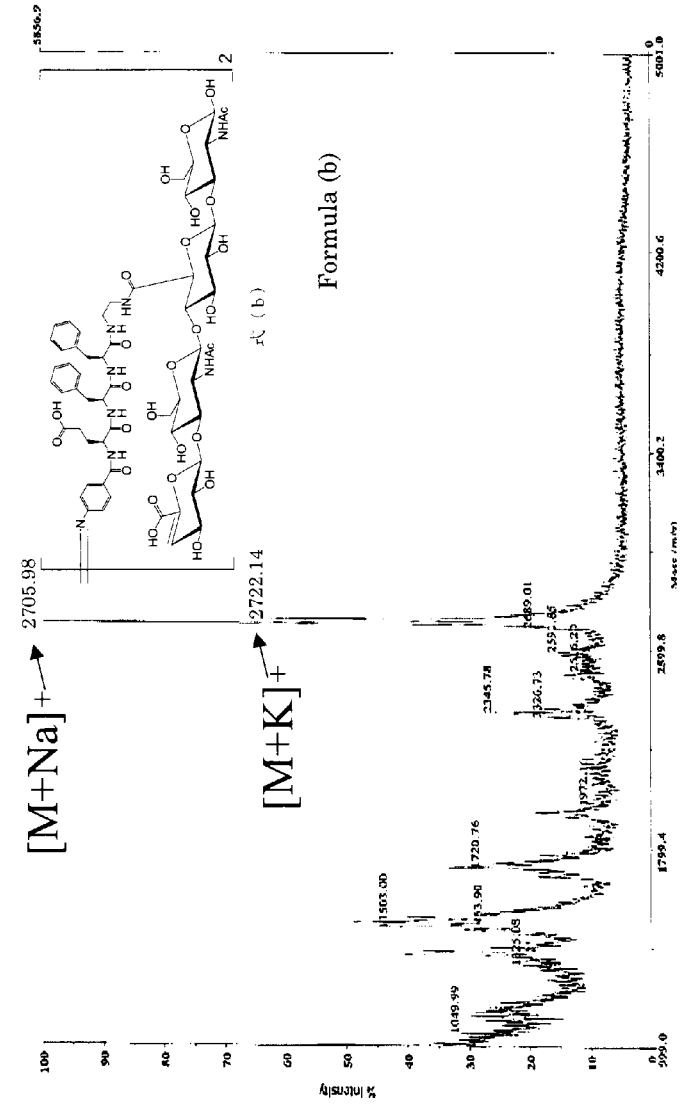
FIG. 4 shows MALDI-TOEMS spectra for fraction F obtained in reverse-phase preparative column chromatography.

Fraction F was further analyzed by MALDI-TOFMS (Voyager DESTR (product of Applied Biosystems); matrix: 10 mg/mL of α-CHCA (0.1% TFA in 50% CH₃CN solution); sampling: 2 μl of the matrix was mixed with 1 μl of fraction F and crystallized on MALDI plate for measurement; detection mode: linear positive). As a result, ions corresponding to sodium- and potassium-added ions of the azo dimmer of pteridine ring free MTX-linker-Δ4 sugar having the structure shown by formula (b) were detected at m/z values of 2705.98 and 2722.14, respectively. (FIG. 4)

Thus, it was suggested that the lysis product obtained by irradiating the HA-MTX conjugate with light and then cleaving the HA chains enzymatically contained substances that were each assumed to be an azo dimmer generated by the binding of two aniline nitrogen atoms resulting from the elimination of the pteridine ring from MTX.

Hence, the results of Examples 2 and 3 supported that reactions A and B presented in FIG. 1 had taken place in the HA-MTX conjugate upon irradiation with light.

Example 4

Example 4 intends to demonstrate the effect of the photostabilizer in the present invention.

(1) Various photostabilizers were examined for their effect on the excitation spectra of the HA-MTX conjugate. Various photostabilizers (methyl p-hydroxybenzoate (methyl paraben), salicylic acid Na, thiosulfuric acid Na, and N-acetyl-tryptophan) were each dissolved in a preparation buffer (0.9% NaCl containing 2 mM phosphate buffer (pH 7.4)) to give a concentration of 9 mg/ml (but 0.9 mg/ml in the case of methyl paraben) and thereafter filtered aseptically by passage through a 0.2-μm filter (Millex GV). A powder of the HA-MTX conjugate prepared in accordance with Production 1 was metered aseptically and dissolved in the filtered, photostabilizer-containing preparation buffer to give a concentration of 1 mg/ml; the thus prepared solutions were used as test samples. To prepare a control solution, the HA-MTX conjugate was dissolved in a photostabilizer-free preparation buffer at a concentration of 1 mg/ml. The test samples and the control were irradiated with light at 300-480 nm and the intensity of fluorescence at 458 nm was measured.

Figure 5:
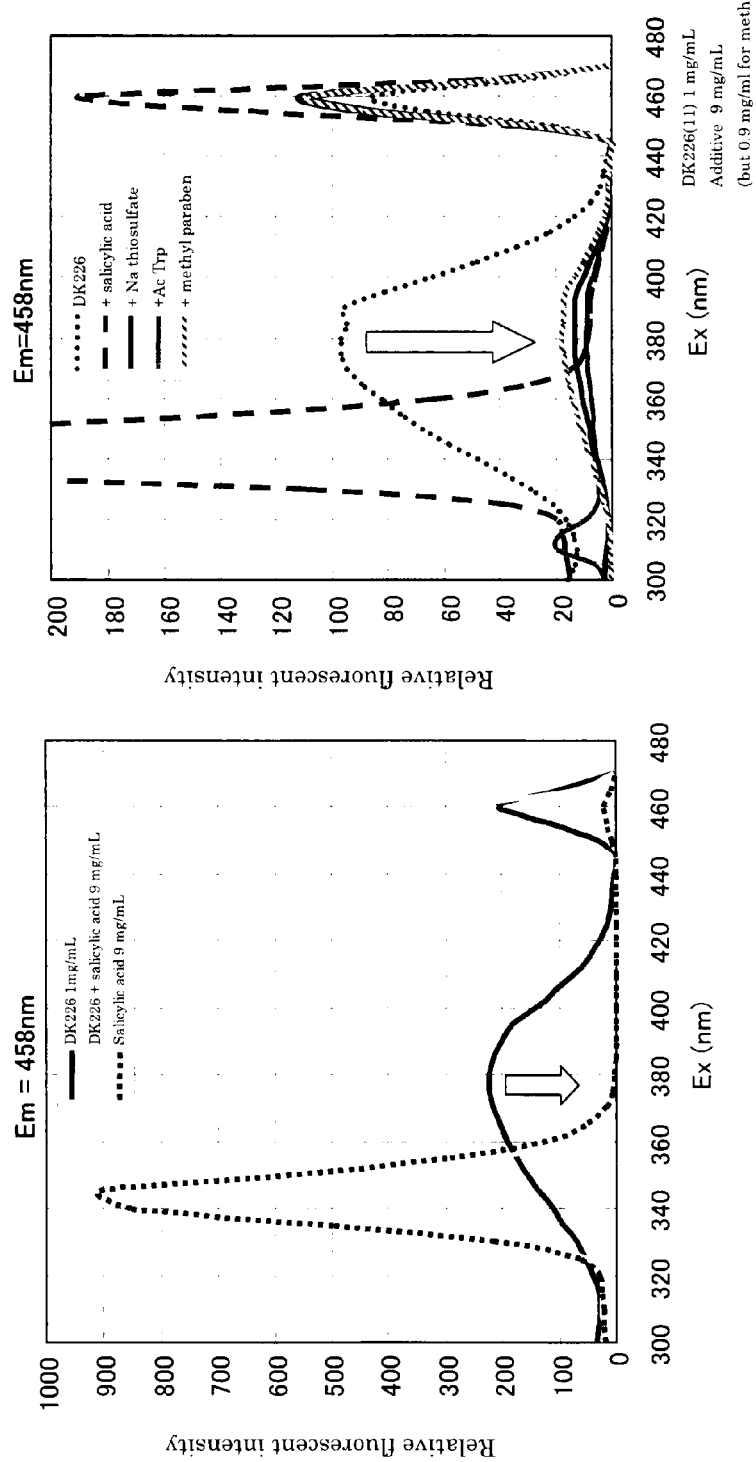
FIG. 5 shows the effects of stabilizers on the excitation spectra of the HA-MTX conjugate.
Figure 6A:
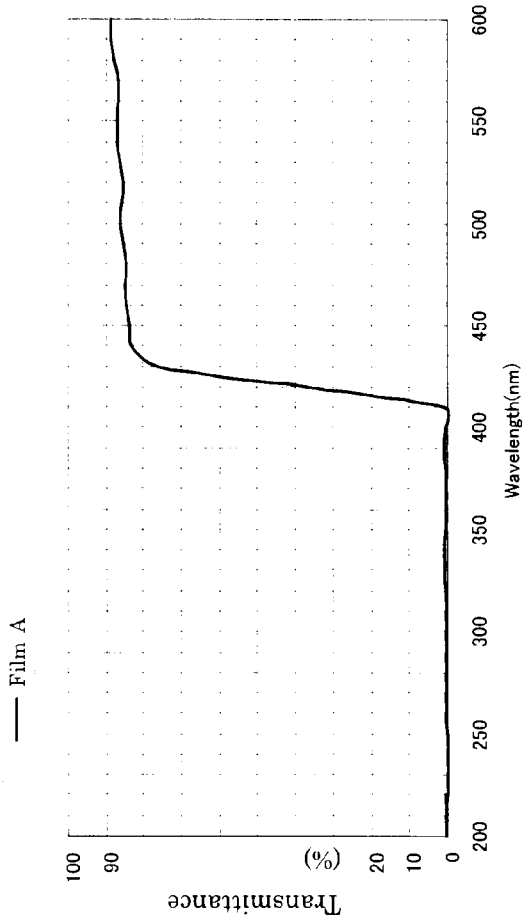
FIG. 6A shows the light transmission through a light-shielding film at varying wavelengths.
Figure 6B:
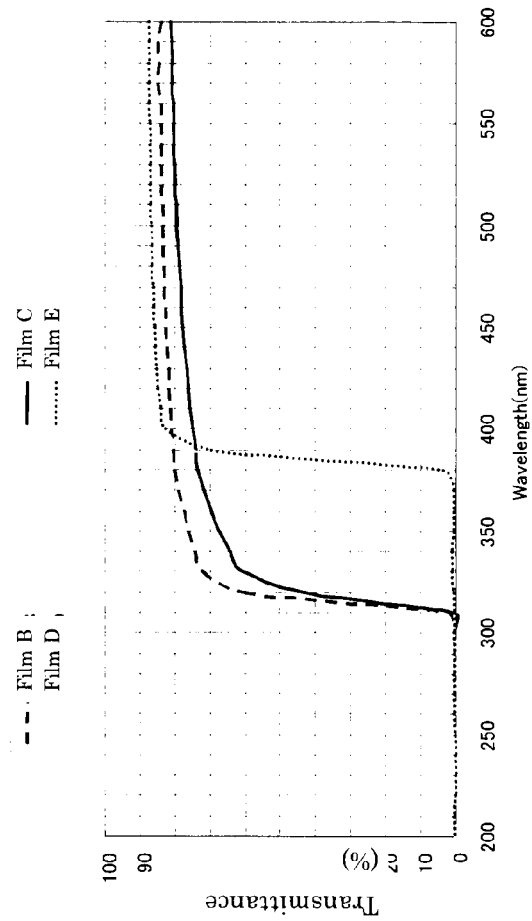
FIG. 6B shows the light transmission through light-shielding films at varying wavelengths.
Figure 6C:
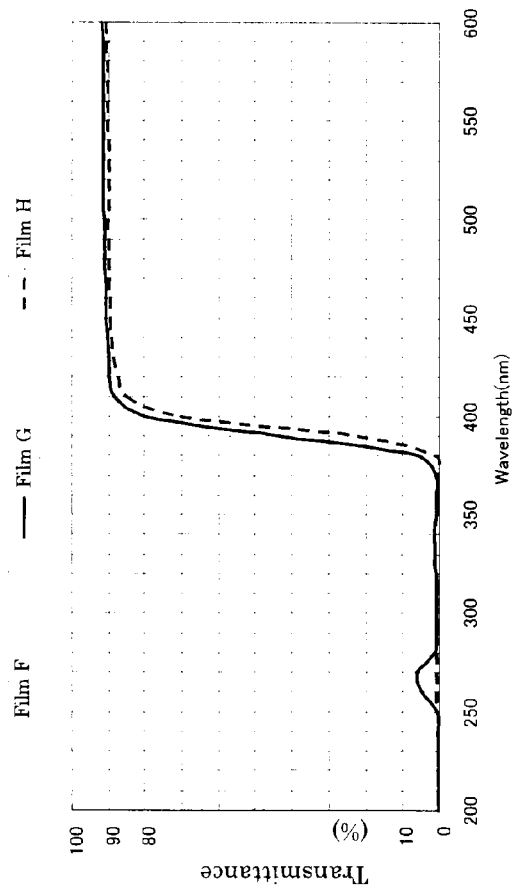
FIG. 6C shows the light transmission through light-shielding films at varying wavelengths.
Figure 6D:
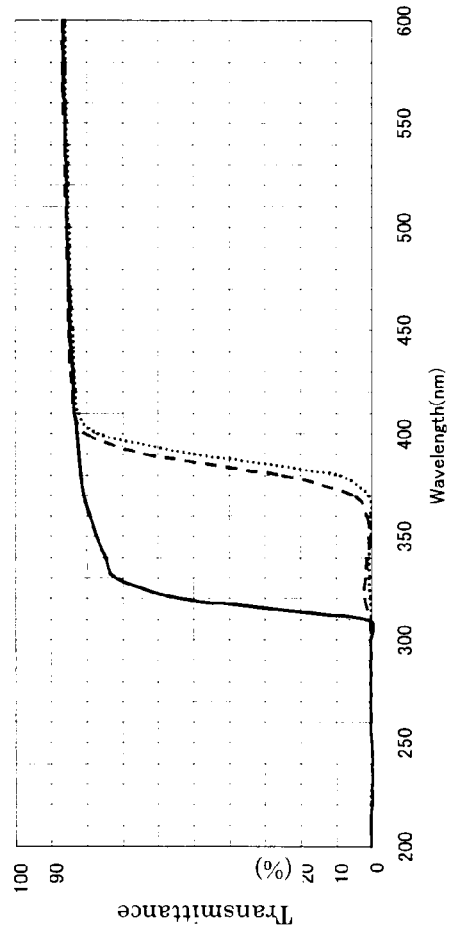
FIG. 6D shows the light transmission through light-shielding films at varying wavelengths.

From the excitation spectra of the control solution shown in FIG. 5, it became clear that the HA-MTX conjugate had main excitation wavelengths in the range of 320-430 nm. The photostabilizers for use in the present invention had a strong quenching action, and even when the HA-MTX conjugate was irradiated with light of excitation wavelengths at which they emitted fluorescence, it was suppressed from fluorescing in the presence of the photostabilizers (see, in particular, the right-hand graph in FIG. 5). Thus, all of the photostabilizers used in the experiment quenched the fluorescence excited from the HA-MTX conjugate in the neighborhood of 320-430 nm (look, in particular, at the excitation maximum wavelength for the HA-MTX conjugate (Ex λmax=380 nm), and the loss of peak due to the addition of the photostabilizers is obvious, indicating suppressed fluorescing) and it is believed that the photostabilizers absorb in some way the excited energy used not only in the emission of fluorescence but also in chemical reactions.

(2) In the next place, the effects of various photostabilizers on the gelation of the HA-MTX conjugate in response to irradiation with light, as well as on the molecular weight and percent conjugation of MTX in the conjugate were studied.

Various photostabilizers (methyl p-hydroxybenzoate (methyl paraben), salicylic acid Na, thiosulfuric acid Na, thioglycolic acid Na, N-acetyltryptophan, and tryptophan) were each dissolved in a preparation buffer (0.9% NaCl containing 2 mM phosphate buffer, pH 7.4) to give a concentration of 1 or 10 mg/ml and thereafter filtered aseptically by passage through a 0.2-μm filter (Millex GV). A powder of the HA-MTX conjugate prepared in accordance with Production 1 was metered aseptically and dissolved in the filtered, photostabilizer-containing preparation buffer to give a concentration of 10 mg/mL; the thus prepared solutions were used as test samples. To prepare a control solution, the HA-MTX conjugate was dissolved in a photostabilizer-free preparation buffer at a concentration of 10 mg/mL.

The thus prepared solutions were put into glass vials not shielded from light and then irradiated with light.

The irradiation was so performed as to give an illuminance of 4000 Lux at 25° C. from a fluorescent lamp for use in a photostability test (TOSHIBA FL20S•D-EDL-D65) by means of a photostability tester (ETAC LABONIC LA110). After the lapse of specified periods (0 h, 25 h, 50 h, 100 h, 150 h, and 300 h) of irradiation, samples were taken and not only checked for gelation but also measured for the molecular weight of the HA-MTX conjugate and the percent conjugation of MTX (in the HA-MTX conjugate).

To evaluate the degree of gelation, the surface of each sample solution was pierced with a spatula and visually checked for the formation of an interface as the result of gelation. In the control, gelation occurred immediately after the start of irradiation with light. On the other hand, gelation was suppressed in all samples to which the photostabilizers had been added. This suppressing effect was recognized even at the point in time of 300-h irradiation. The molecular weight and percent MTX conjugation of the HA-MTX conjugate as analyzed by gel filtration chromatography are shown in Tables 3A and 3B, respectively. The apparatus used in gel filtration chromatography was equipped with OHpackSB-806HQ (Shodex) as a column, RI-71 (Shodex) as an IR detector, and 875-UV (JASCO, detection wavelength: 304 nm) as a UV detector and analysis was conducted under the following conditions. Eluent: 50 mM sodium phosphate aqueous solution (pH 6.0); elution rate: 0.6 mL/min; column temperature: 40° C. By the above-described gel filtration chromatography, the elution times of the conjugate of interest were determined and the molecular weight of the same conjugate was determined from the relationship between the elution times and molecular weights of standard substances. As the standard substances, hyaluronic acid samples were prepared in varying molecular weights and their accurate values were calculated by the limiting viscosity method before it was used. The percent conjugation of MTX in the respective samples at 0 h varied in the range of 2.1-2.3% but this range of variations is normally observed in the measurement of percent MTX conjugation.

TABLE 3A

Lapse in Time of the Molecular Weight of Samples Not Shielded from Light

| Additive | | Molecular weight ($\times 10^4$) Irradiation time | | | | | |
|---|---|---|---|---|---|---|---|
| Type | Conc. (mg/ml) | 0 h | 25 h | 50 h | 100 h | 150 h | 300 h |
| Not added | 0 | NT | Gelled → Measurement impossible | | | | |
| Methyl paraben | 1 | 187 | 155 | 127 | 107 | 126 | 65 |
| Na salicylate | 10 | 185 | 176 | 182 | 176 | 170 | 149 |
|  | 1 | 186 | 172 | 122 | 85 | 69 | 22 |
| Na thiosulfate | 10 | 190 | 190 | 182 | 171 | 150 | 176 |
|  | 1 | 181 | 145 | 28 | 4 | 3 | 2 |
| Na thioglycolate | 10 | 181 | 166 | 169 | 163 | 154 | 5 |
|  | 1 | 163 | 136 | 97 | 8 | 5 | 2 |
| N-acetyltryptophan | 10 | 190 | 180 | 175 | 146 | 135 | 97 |
|  | 1 | 178 | 164 | 166 | 138 | 128 | 78 |
| Tryptophan | 10 | 181 | 175 | 164 | 118 | 110 | 70 |
|  | 1 | 188 | 171 | 138 | 112 | 83 | 45 |

NT: not tested;
*Measurement was impossible on account of gelation.

TABLE 3B

Lapse in Time of the Percent Conjugation of MTX in Samples Not Shielded from Light

| Additive | | Percent Conjugation (%) | | | | | |
|---|---|---|---|---|---|---|---|
| Type | Conc. (mg/ml) | 0 h | 25 h | 50 h | 100 h | 150 h | 300 h |
| Not added | 0 | NT | Gelled → Measurement impossible | | | | |
| Methyl paraben | 1 | 2.2 | 2.0 | 2.1 | 2.0 | 2.1 | 1.9 |
| Na salicylate | 10 | 2.2 | 2.2 | 2.1 | 2.1 | 2.2 | 2.2 |
|  | 1 | 2.2 | 2.2 | 2.1 | 1.9 | 1.8 | 2.0 |
| Na thiosulfate | 10 | 2.1 | 2.2 | 2.3 | 2.1 | 2.2 | 2.1 |
|  | 1 | 2.3 | 2.1 | 1.5 | 0.8 | 0.6 | 0.4 |
| Na thioglycolate | 10 | 2.1 | 2.2 | 2.3 | 2.0 | 2.2 | 1.4 |
|  | 1 | 2.1 | 2.2 | 2.2 | 1.4 | 1.0 | 0.4 |
| N-acetyltryptophan | 10 | 2.2 | 2.2 | 2.2 | 1.9 | 2.1 | 2.0 |
|  | 1 | 2.2 | 2.2 | 2.3 | 2.2 | 2.1 | 2.1 |
| Tryptophan | 10 | 2.2 | 2.3 | 2.2 | 2.2 | 2.2 | 2.2 |
|  | 1 | 2.2 | 2.2 | 2.2 | 2.2 | 2.1 | 2.2 |

NT: not tested;
*Measurement was impossible on account of gelation.

According to the guidelines for photoaccelerated testing (ICH module 3/Q1B), a sample under photostability test must be exposed to light from a light source designed to provide an output satisfying the radiation reference for D65 (internationally approved as a standard for the outdoor daylight specified in ISO 10977) or ID65 in such a way as to give a total illuminance of $120 \times 10^4$ Lux·h and a total near ultraviolet radiation energy of 200 W·h/m² and more. If the sample is found to be low in photostability, it must be shielded from light or otherwise treated to ensure adequate photostability.

However, the purpose of the present invention is to secure stability in the case where exposure to light occurs in the manufacturing process or in the practice at hospitals and medical settings where packaged drugs are stripped of the package and left to stand for several days until use, and it is not considered necessary to meet the hostile test conditions set forth in the guidelines mentioned above. To attain the object of the present invention, it would suffice if the pharmaceutical preparation is assured to remain stable even when it is irradiated with light at an illuminance of 4000 Lux for about 50-100 hours. On the following pages, this criterion will be used to evaluate photostability.

For detailed information about the guidelines for photoaccelerated testing (ICH module 3/Q1B), reference should be made to the following document.

"On Guidelines for Photostability Testing of New Drug Substances and New Preparations", Notification No. 422, May 28, 1997 from the Director of Examination Division, Pharmaceutical Affairs Bureau, Ministry of Health and Welfare (addressed to the Director of Central Hygiene Department of Relevant Local Government); or ICH Harmoised Tripartite Guideline, Stability Testing: PHOTOSTABILITY TESTING OF NEW DRUG SUBSTANCES AND PRODUCTS, Recommended for Adoption at Step 4 of the ICH process on 6 Nov. 1996 by the ICH Steering Committee.

According to Tables 3A and 3B, the photostabilizers have not only the above-described gelation suppressing effect but also the ability to suppress the drops in the molecular weight of the HA-MTX conjugate and the percent conjugation of MTX in the conjugate. In particular, when sodium salicylate, sodium thiosulfate and sodium thioglycolate were each added at a concentration of 10 mg/ml, they proved considerably effective in suppressing drops in the molecular weight and percent conjugation even when the time of irradiation exceeded 100 hours. Further, methyl paraben, N-acetyltryptophan, and tryptophan, even when they were added at a lower concentration (1 mg/mL), could suppress drops in the molecular weight and percent conjugation for irradiation periods that did not exceed about 100 hours.

Example 5

Example 5 demonstrates the ability of films blocking light at specified wavelengths to inhibit the gelation of the HA-MTX conjugate.

Films

As already described in Examples 1 and 4, the HA-MTX conjugate fluoresced upon irradiation with light, particularly at wavelengths of 320-430 nm. Therefore, in Example 5, verification was performed using films that would mainly block light having wavelengths in that range or its neighborhood. The light transmittance of the tested films at varying wavelengths was measured with a spectrophotometer (product of Hitachi, Ltd.; double-beam spectrophotometer of Model U-2000; data mode, % T; scan speed, 400 nm/min). The results are shown in FIGS. 6A to 6D.

Film A: UV Guard (product of FUJIFILM Corporation; 70 µm)
Film B: TEIJIN™ TETRON™ Film S (product of Teijin DuPont Films; 25 µm)
Film C: TEIJIN™ TETRON™ Film S (product of Teijin DuPont Films; 50 µm)
Film D: TEIJIN™ TETRON™ Film HB (product of Teijin DuPont Films; 25 µm)
Film E: TEIJIN™ TETRON™ Film HB (product of Teijin DuPont Films; 50 µm)
Film F: DENKA DX FILM™ DX14S Series (product of Denki Kagaku Kogyo; DX14S0230; 30 µm)
Film G: DENKA DX FILM™ DX14S Series (product of Denki Kagaku Kogyo; DX14S0250; 50 µm)
Film H: DENKA DX FILM™ DX14S Series (product of Denki Kagaku Kogyo; DX14S02100; 100 µm)
Film I: Polyester film, LUMILAR™ (product of Toray Industries, Inc.; 25 µm)
Film J: Polyester film, LUMILAR™ (product of Toray Industries, Inc.; 50 µm)
Film K: UV absorbing polyester film, T-UV™ (product of TOCHISEN; 25 µm)
Film L: UV absorbing polyester film, T-UV™ (product of TOCHISEN; 50 µm).

As FIGS. 6A to 6D show, each of the films tested could at least block light having wavelengths of no more than 300 nm. In particular, UV Guard (product of FUJIFILM Corporation) blocked light of wavelengths of 410 nm and shorter while suppressing the transmittance of wavelengths at 420 nm and shorter to 50% and less. In other words, the film is not only characterized by blocking the wavelengths (310 nm, 360 nm, and 405 nm) that caused the HA-MTX conjugate to gel in Example 1 but also characterized by suppressing the transmittance of light in the wavelength range (320-430 nm) where the HA-MTX conjugate fluoresced.

Gelling Test

Next, the above-described films were tested for their ability to suppress the HA-MTX conjugate from gelling. A HA-MTX conjugate DK-226 (molecular weight: 207×10$^4$; percent conjugation: 2.2%) prepared by a modification of the method described in Example 2 was dissolved in 0.9% NaCl containing 2 mM phosphate buffer (pH 7.3) to prepare a solution of the HA-MTX conjugate whose concentration was 9.9 mg/ml in terms of HA. Glass vials around which the above-described films were wound were filled with 250-µl portions of the solution. Each vial was put into an incubator and irradiated with light (illuminance: 3600 lux) from a fluorescent lamp for use in a photostability test (TOSHIBA FL20S•D-EDL-D65) at 25° C. and the degree of gelation was visually checked. The results are shown in Table 4 below.

TABLE 4

Gelation in Containers Wrapped with Various Films

| Manufacturer | Film | Thickness (µm) | Material | State of gelation | | | | | | | |
|---|---|---|---|---|---|---|---|---|---|---|---|
| | | | | 1 h | 2 h | 3 h | 4 h | 5 h | 6 h | 8 h | 10 h | 12 h |
| | None | | | ± | + | + | + | + | | | | |
| FUJI FILM CORPORATION | UV Guard (Film A) | 40 | PET | − | − | − | − | − | − | − | − | + |
| TEIJIN DUPONFILMS | S-25 (Film B) | 25 | Polyester | − | + | + | + | + | | | | |
| | S-50 (Film C) | 50 | | − | + | + | + | + | | | | |
| | HB-25 (Film D) | 25 | | − | − | + | + | + | | | | |
| | HB-50 (Film E) | 50 | | − | − | + | + | + | | | | |

TABLE 4-continued

Gelation in Containers Wrapped with Various Films

| Manufacturer | Film | Thickness (μm) | Material | State of gelation | | | | | | | |
|---|---|---|---|---|---|---|---|---|---|---|---|
| | | | | 1 h | 2 h | 3 h | 4 h | 5 h | 6 h | 8 h | 10 h | 12 h |
| Toray Industries | LUMILAR (Film I) | 25 | Polyester | − | + | + | + | + | | | |
| | LUMILAR (Film J) | 50 | | − | + | + | + | + | | | |
| TOCHISEN | T-UV (Film K) | 25 | | − | − | + | + | + | | | |
| | T-UV (Film L) | 50 | | − | − | + | + | + | | | |
| DENKI KAGAKU KOGYO | DX-14S0230 (Film F) | 30 | PVDF | − | ± | + | + | + | | | |
| | DX-14S0250 (Film G) | 50 | | − | ± | + | + | + | | | |
| | DX-14S02100 (Film H) | 100 | | − | ± | + | + | + | | | |
| | DX-14S02100 (dual) | 200 | | − | − | + | + | + | | | |
| | DX-14S02100 (quadruple) | 400 | | − | − | − | ± | + | | | |

− no gelation
± medium
+ gelation

All films extended the time-to-gel compared to the control using no such films.

HB-25 and HB-50 suppressed gelation for periods not exceeding about 2 hours. S-25 and S-50 suppressed gelation up until about an hour passed. Use of UV Guard (FUJIFILM CORPORATION) was the most effective in delaying delation and it suppressed gelation up until about 10 hours passed.

Considering the period of time for which gelation was suppressed and the characteristic light transmittance vs. wavelength relationship of each film (as shown in FIGS. 6A to 6D), it is preferred for the purpose of delaying gelation in practical applications to suppress the light transmittance at wavelengths of 300 nm and shorter, more preferred to suppress the light transmittance at wavelengths of 370 nm and shorter, and most preferred to block light at 410 nm and shorter.

On the other hand, considering the above observations together with the results of Example 1 that suggest the close relationship between gelation and fluorescing, it is believed that in order to delay gelation most effectively, wavelengths in the range of 320-430 nm that cause fluorescing, more preferably, wavelengths in a wider range should be blocked.

Figure 7:
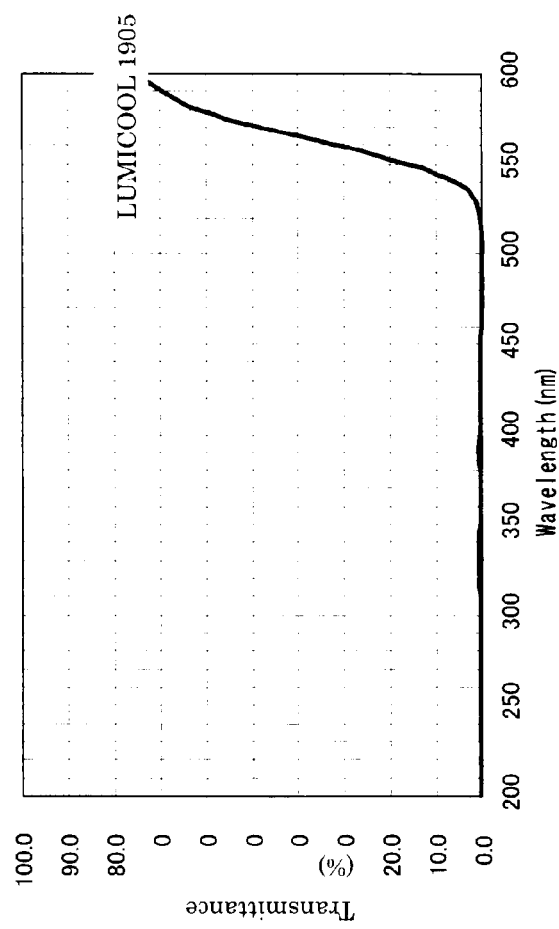
FIG. 7 shows the light transmission through a light-shielding film at varying wavelengths.

As a matter of fact, gelation was delayed by suppressing the transmittance of light at wavelengths of 300 nm and shorter but the effect was not completely satisfactory; on the other hand, when the same test was conducted as described above, except for using a film blocking light of 540 nm and shorter (LUMICOOL™ 1905 produced by Lintec Corporation and capable of blocking a range of wavelengths at 540 nm and shorter; see FIG. 7), gelation was suppressed for as long as 10 days, as shown in Table 5. Therefore, to suppress gelation, it is effective to suppress (preferably block) light of 320-430 nm, preferably light of 540 nm and shorter.

Example 6

Next, using a vial wrapped with (LUNICOOL™ 1905 (a brown film produced by Lintec Corporation; see FIG. 7) which was one of the films employed in Example 5, a test was conducted in the same manner as described in Example 4(2). As a control simulating complete blocking of light, a vial containing a photostabilizer-free sample was covered with aluminum foil.

In this experiment, neither sample was recognized to have gelled. From the result of this experiment, it was verified that by additional use of the film capable of blocking light of wavelengths in the range presumably responsible for gelation and a decrease in molecular weight, namely, 320-430 nm, preferably 540 nm and shorter (the film was LUMICOOL™ 1905 characterized by blocking wavelengths of 540 nm and shorter), gelation and a drop in molecular weight could be suppressed and stable quality could be retained even after the passage of 300 hours. It was also verified that the result was comparable to that obtained by using aluminum foil to assure complete blocking of light.

Shown below are the results of measuring the molecular weight of the HA-MTX conjugate and the percent conjugation of MTX (the molecular weight and percent conjugation measurements were in accordance with the description of Production 1).

TABLE 6

Results of Measurements on Samples Additionally Using Light-shielding Film (LUMICOOL ™ 1905)

| Additive | | Molecular weight ($\times 10^4$) | | | Percent Conjugation (%) | | |
|---|---|---|---|---|---|---|---|
| | | Irradiation time | | | Irradiation time | | |
| Type | Conc. (mg/mL) | 0 h | 150 h | 300 h | 0 h | 150 h | 300 h |
| Methyl paraben | 1 | 187 | 184 | 179 | 2.2 | 2.2 | 2.2 |

TABLE 5

| | State of gelation | | | | | | | | | | | | | |
|---|---|---|---|---|---|---|---|---|---|---|---|---|---|---|
| | 1 d | | | | | | | | | 2 d | | 3 d | | |
| Film | 1 h | 2 h | 5 h | 6 h | 7 h | 8 h | 10 h | 11 h | 12 h | 24 h | 48 h | 56 h | 4 d | 6 d | 8 d | 10 d |
| None | ± | + | + | + | + | + | | | + | + | + | + | + | + | + |
| LUMICOOL 1905 | − | − | − | − | − | − | | | | − | | − | − | − | − | − |

TABLE 6-continued

Results of Measurements on Samples Additionally Using
Light-shielding Film (LUMICOOL ™ 1905)

| Additive Type | Conc. (mg/mL) | Molecular weight (×10⁴) Irradiation time | | | Percent Conjugation (%) Irradiation time | | |
|---|---|---|---|---|---|---|---|
| | | 0 h | 150 h | 300 h | 0 h | 150 h | 300 h |
| Na salicylate | 10 | 185 | 190 | 179 | 2.2 | 2.2 | 2.1 |
| | 1 | 186 | 184 | 163 | 2.2 | 2.1 | 2.2 |
| Na thiosulfate | 10 | 190 | 188 | 186 | 2.1 | 2.2 | 2.1 |
| | 1 | 181 | 186 | 180 | 2.3 | 2.2 | 2.2 |
| Na thioglycolate | 10 | 181 | 170 | 157 | 2.1 | 2.1 | 2.2 |
| | 1 | 163 | 123 | 44 | 2.1 | 2.2 | 2.2 |
| N-acetyl-tryptophan | 10 | 190 | 186 | 187 | 2.2 | 2.2 | 2.2 |
| | 1 | 178 | 172 | 136 | 2.2 | 2.3 | 2.2 |
| Tryptophan | 10 | 181 | 177 | 156 | 2.2 | 2.2 | 2.2 |
| | 1 | 188 | 176 | 153 | 2.2 | 2.2 | 2.2 |
| Control (Al-shielded) | — | 190 | 190 | 184 | 2.2 | 2.2 | 2.3 |

As Table 6 shows, the additional use of the light-shielding film was recognized to provide even greater suppressing effects on gelation and a drop in molecular weight. In other words, it became clear that the suppressing effects on the drop in molecular weight and the drop in percent conjugation were great in all samples. In particular, methyl paraben, sodium salicylate and sodium thiosulfate, at whichever concentrations they were used, showed stabilizing effects (suppressing effects on the drop in molecular weight and the drop in percent conjugation of MTX) that were comparable to those obtained in the case where complete shielding of light was ensured by aluminum foil (i.e., the control).

The invention claimed is:

1. A photostabilized pharmaceutical composition comprising a conjugate of hyaluronic acid (HA) or a hyaluronic acid derivative and methotrexate (MTX) or a salt of the conjugate, and a photostabilizer, wherein the HA or its derivative and the MTX are conjugated via a linker which contains at least one amino acid and, optionally, a part represented by other than amino acids,
   wherein the photostabilizier is at least one compound selected from the group consisting of thiosulfuric acid, sodium thiosulfate, thioglycolic acid, ammonium thioglycolate, sodium thioglycolate, potassium thioglycolate, ethyl thioglycolate, thiomalic acid, ammonium thiomalate, sodium thiomalate, potassium thiomalate, mercaptopropionic acid, ammonium mercaptopropionate, sodium mercaptopropionate, potassium mercaptopropionate; N-acetyltryptophan or a salt thereof, tryptophan or a salt thereof, tryptophan methyl ester or a salt thereof, tryptophan ethyl ester or a salt thereof, tyrosine or a salt thereof, phenylalanine or a salt thereof, 4-hydroxybenzoic acid, sodium 4-hydroxybenzoate, 3-hydroxybenzoic acid, and sodium 3-hydroxybenzoate,
   wherein the photostabilizer is not linked to the conjugate in the pharmaceutical composition.

2. The pharmaceutical composition according to claim 1, wherein the photostabilizer is a quencher or a radical scavenger.

3. The pharmaceutical composition according to claim 1, comprising from 0.01 to 30% (w/v) of the photostabilizer.

4. A medicine comprising the pharmaceutical composition according to claim 1, wherein the medicine is wrapped with a packaging material that at least blocks light over the entire wavelength region of light in a range of from 320 to 430 nm, wherein the packaging material does not block or attenuate light having at least part of the wavelengths not included within said range.

5. The medicine according to claim 4, wherein the packaging material at least blocks light over the entire wavelength region of light not exceeding 540 nm.

6. The medicine according to claim 4, wherein the packaging material at least blocks light over the entire wavelength region of light not exceeding 540 nm.

7. The pharmaceutical composition according to claim 1, wherein the photostabilizer is at least one compound selected from the group consisting of thiosulfuric acid, sodium thiosulfate, thioglycolic acid, ammonium thioglycolate, sodium thioglycolate, potassium thioglycolate, ethyl thioglycolate, N-acetyltryptophan or a salt thereof, and tryptophan or a salt thereof.

8. The pharmaceutical composition according to claim 1, wherein the linker contains a peptide chain comprising from 1 to 8 amino acids and a $C_{2-20}$ alkylenediamine chain into which from 1 to 5 oxygen atoms are optionally inserted and/or which is optionally substituted by a carboxyl group or a $C_{1-6}$ alkoxycarbonyl group.

9. The pharmaceutical composition according to claim 1, wherein the composition is prepared by mixing the conjugate and a solution of the photostabilizer.

* * * * *